(12) United States Patent
Balzarini et al.

(10) Patent No.: US 8,912,163 B2
(45) Date of Patent: Dec. 16, 2014

(54) COMPOSITIONS FOR THE TREATMENT OR PROPHYLAXIS OF VIRAL INFECTIONS

(71) Applicants: Katholieke Universiteit Leuven, Leuven (BE); Consejo Superior de Investigaciones Ceintificas, Madrid (ES)

(72) Inventors: Jan Balzarini, Heverlee (BE); Maria Jose Camarasa, Madrid (ES); Sonsoles Velazquez, Madrid (ES)

(73) Assignees: Katholieke Universiteit Leuven, Leuven (BE); Consejo Superior de Investigaciones Ceintificas, Madrid (ES)

(*) Notice: Subject to any disclaimer, the term of this patent is extended or adjusted under 35 U.S.C. 154(b) by 0 days.

(21) Appl. No.: 13/971,631

(22) Filed: Aug. 20, 2013

(65) Prior Publication Data

US 2013/0338096 A1 Dec. 19, 2013

Related U.S. Application Data

(62) Division of application No. 12/676,394, filed as application No. PCT/EP2008/007009 on Aug. 27, 2008, now Pat. No. 8,513,215.

(30) Foreign Application Priority Data

Sep. 7, 2007 (GB) .................................. 0717526.8

(51) Int. Cl.
| | | |
|---|---|---|
| *C07H 23/00* | (2006.01) | |
| *C07H 19/24* | (2006.01) | |
| *C07K 5/083* | (2006.01) | |
| *C07K 9/00* | (2006.01) | |
| *A61K 47/48* | (2006.01) | |

(52) U.S. Cl.
CPC .............. *C07H 23/00* (2013.01); *C07K 5/0808* (2013.01); *C07K 9/003* (2013.01); *A61K 47/48246* (2013.01); *C07H 19/24* (2013.01); *A61K 47/48038* (2013.01)
USPC ......................................... 514/49; 536/27.13

(58) Field of Classification Search
USPC ......................................... 514/27.13; 536/49
See application file for complete search history.

(56) References Cited

U.S. PATENT DOCUMENTS 7,585,851 B2 * 9/2009 Bryant et al. .................. 514/49

OTHER PUBLICATIONS

Merck Manual, 16th Ed., 1992, pp. 183-189.*
Angell et al, Bioorganic & Medicinal Chemistry Letters, 2004, 14, 2397-2399.*

* cited by examiner

*Primary Examiner* — Ganapathy Krishnan
(74) *Attorney, Agent, or Firm* — Cooley LLP; Ivor R. Elrifi; Heidi A. Erlacher

(57) ABSTRACT

A compound of the general formula (III): wherein X is O, S, NH or $CH_2$; Y is O, S or NH; Z is O, S or $CH_2$; $R_1$ is $C_{1-8}$ alkyl, especially $C_{1-6}$ alkyl, preferably n-alkyl, e.g., n-pentyl or n-hexyl; at least one of $R_2$ and $R_3$ is H—$[R_4$—$R_5]_n$—$R_6$—, in which: H—$[R_4$—$R_5]_n$— comprises an oligopeptide, $R_4$ being an amino acid and $R_5$ being an amino acid selected from proline, alanine, hydroxyproline, dihydroxyproline, thiazolidinecarboxylic acid (thioproline), dehydroproline, pipecolic acid (L-homoproline), azetidinecarboxylic acid, aziridinecarboxylic acid, glycine, serine, valine, leucine, isoleucine and threonine, $R_6$ is a neutral, non-polar amino acid moiety that is bonded to $R_5$ by a peptide bond, and n is 1, 2, 3, 4 or 5; and the other of $R_3$ and $R_2$ is H—$[R_4$—$R_5]$n-$R_6$— or H; or a pharmaceutically acceptable salt thereof.

22 Claims, 2 Drawing Sheets

COMPOSITIONS FOR THE TREATMENT OR PROPHYLAXIS OF VIRAL INFECTIONS

RELATED APPLICATIONS

This application is a divisional application of U.S. patent application Ser. No. 12/676,394, filed on Jun. 8, 2010 which is a national stage application, filed under 35 U.S.C. §371, of International Application No. PCT/EP2008/007009, filed on Aug. 27, 2008, which claims the benefit of priority of GB 0717526.8, filed on Sep. 7, 2007, the contents of each of which are incorporated herein by reference in their entireties.

The present invention provides improvements in or relating to compositions for the treatment or prophylaxis of viral infections such, for example, as those caused by the Varicella Zoster virus (VZV). Varicella Zoster virus is the aetiological agent of chickenpox and shingles, which can cause considerable human illness and suffering.

WO 01/83501 A1, the contents of which are incorporated herein by reference, discloses certain nucleoside analogues with potent activity against Varicella Zoster virus (VZV), said nucleoside analogues having the general formula (I):

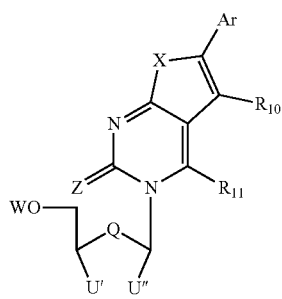

(I)

wherein:

Ar is an, optionally substituted, aromatic ring system, the aromatic ring system comprising one six-membered aromatic ring or two fused six-membered aromatic rings;

$R_{10}$ and $R_{11}$ are each independently selected from the group comprising hydrogen, alkyl, cycloalkyl, halogens, amino, alkylamino, dialkylamino, nitro, cyano, alkyloxy, aryloxy, thiol, alkylthiol, arylthiol, aryl;

Q is selected from the group comprising O, S and $CY_2$, where Y may be the same or different and is selected from H, alkyl and halogens;

X is selected from the group comprising O, NH, S, N-alkyl, $(CH_2)_m$ where m is 1 to 10, and $CY_2$ where Y may be the same or different and is selected from hydrogen, alkyl and halogens;

Z is selected from the group comprising O, S, NH, and N-alkyl;

U" is H and U' is selected from H and $CH_2T$, or U' and U" are joined so as to form a ring moiety including Q wherein U'-U" together is respectively selected from the group comprising CT'H-CT'T" and CT'=CT', so as to provide ring moieties selected from the group comprising:

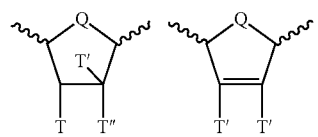

wherein T is selected from the group comprising OH, H, halogens, O-alkyl, O-acyl, O-aryl, CN, $NH_2$ and $N_3$;

T' is selected from the group comprising H and halogens and, where more than one T' is present, they may be the same or different;

T" is selected from the group comprising H and halogens; and

W is selected from the group comprising H, a phosphate group and a phosphonate group;

with the proviso that when T is OAc and T' and T" are present and are H, Ar is not 4-(2-benzoxazolyl)phenyl.

According to WO 01/83501 A1, W may be modified to provide any pharmacologically acceptable salt or derivative of H, phosphate or phosphonate. WO 01/83501 A1 further discloses that when W is selected from phosphates and derivatives thereof and phosphonates and derivatives thereof, W may be modified to provide a pro-drug of the compound of formula (I).

Compounds 1 and 2 below are particularly preferred compounds according to WO 01/83501 A1:

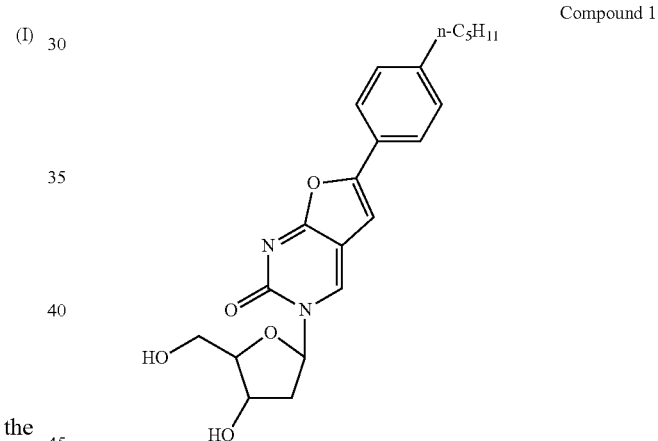

Compound 1

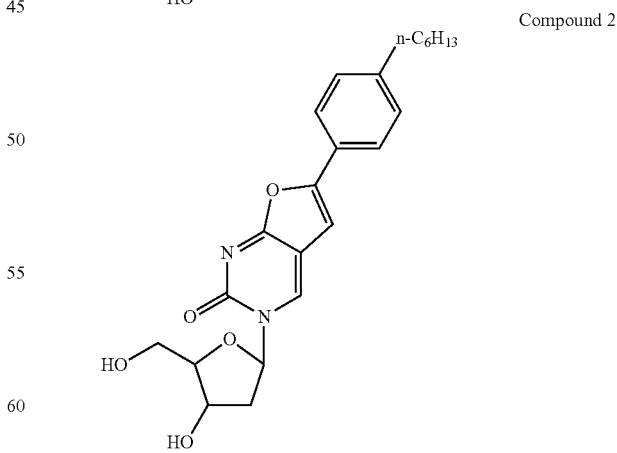

Compound 2

The development of many promising therapeutic agents is hindered by their poor water solubility.

WO 2004/098644 A1, the contents of which are also incorporated herein by reference, discloses conjugates of therapeutic agents with a peptidic moiety in which the conjugate is cleavable by a dipeptidyl-peptidase, such as CD26. Such conjugation of the therapeutic agents is calculated to ameliorate their solubility and bioavailability, and may be used to modulate the protein binding of a therapeutic compound and to target specific sites in a mammal.

By "CD26" as used herein is meant dipeptidyl-peptidase IV (EC 3.4.14.5) in its membrane bound or free form; synonyms for CD26 are DPPIV, DPP4, CD26/DPPIV, or ADCP2 (adenosine deaminase complexing protein 2). A dipeptidyl-peptidase is an enzyme with a dipeptidyl aminopeptidase activity, i.e., removing a dipeptide from the amino-terminal side of a substrate site by cleavage of the second CO—NH amide bond in the substrate. Other enzymes than CD26 with a comparable activity and proteolytic specificity as CD26 (i.e., prolyloligopeptidases) are referred to by "dipeptidyl-peptidase(s)". "Dipeptidylpeptidase IV" refers to CD26.

According to WO 2004/098644 A1, a therapeutic compound having, or being bound to a linker $A_m$ having an amino group, particularly a terminal primary or secondary amino group, capable of binding with the carboxyl group of an amino acid is linked to an oligopeptide consisting of a general structure H—[X—Y]$_n$, wherein X is an amino acid, n is between 1 and 5 and Y is an amino acid selected from proline, alanine, hydroxyproline, dihydroxyproline, thiazolidinecarboxylic acid (thioproline), dehydroproline, pipecolic acid (L-homoproline), azetidinecarboxylic acid, aziridinecarboxylic acid, glycine, serine, valine, leucine, isoleucine and threonine, and wherein the binding between the carboxy terminus of H—[X—Y]$_n$ and the amino group of the therapeutic compound or its linker occurs via an amide. In one embodiment, the peptide has between two to five CD26 cleavable repeats. In another embodiment, the number m of amino acids in the linker $A_m$ is between 1 and 15, more particularly between 1 to 3. A may be any amino acid. More particularly, m is 1 and A is valine.

International patent application no. PCT/GB2007/001677, which is comprised in the state of the art according to EPCa.54(3) and the contents of which are also incorporated herein by reference, discloses a compound of general formula (II):

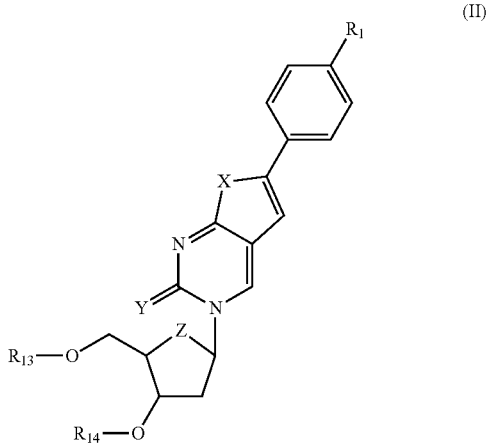

(II)

wherein X is O, S, NH or $CH_2$,
Y is O, S or NH,
Z is O, S or $CH_2$,
$R_1$ is $C_{1-6}$ alkyl, preferably n-alkyl, e.g., n-pentyl or n-hexyl, and
one of $R_{13}$ and $R_{14}$ is OH, and the other of $R_{14}$ and $R_{13}$ is a neutral, non-polar amino acid moiety,
or a pharmaceutically acceptable salt or hydrate thereof.
Preferably $R_{13}$ or $R_{14}$ is valine, especially L-valine.

The compound of PCT/GB2007/001677 is especially suitable for oral administration. It has been shown that the oral bioavailability of drugs can be mediated by amino acid prodrug derivatives containing an amino acid, preferably in the L-configuration. L-valine seems to have the optimal combination of chain length and branching at the β-carbon of the amino acid for intestinal absorption. hPEPT-1 has been found to be implicated as the primary absorption pathway of increased systemic delivery of L-valine ester prodrugs. The hPEPT-1 transport needs to interact optimally with a free $NH_2$, a carbonyl group and a lipophylic entity, and may form additional H-bridges with its target molecule.

Preferred compounds according to PCT/GB2007/001677 are:

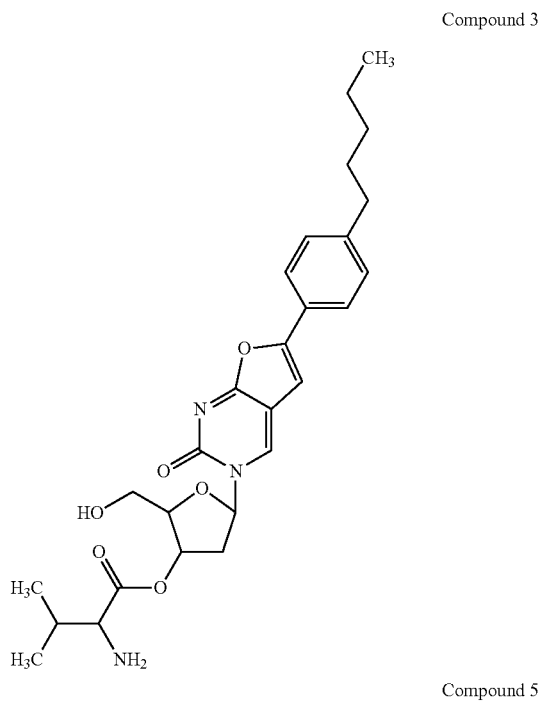

Compound 3

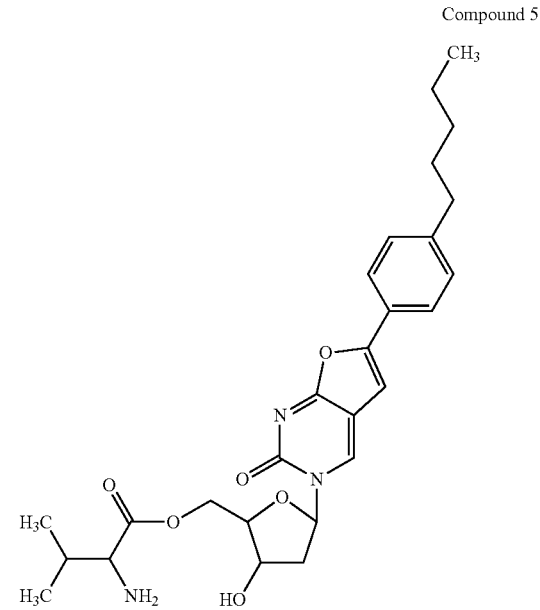

Compound 5

Compound 5 was found to have improved bioavailability after oral dosing in mice as compared to Compound 1 of WO 01/83501 A1 (see above).

It has now been found that by conjugating the compound of PCT/GB2007/001677 with a CD26 cleavable oligopeptide, a surprisingly great improvement in the solubility of the compound as compared with the non-derivatised nucleoside analogue of general formula (I) according to WO 01/83501 A1 may be obtained, without adversely affecting the bioavailability of such compound. Indeed, the bioavailability may even be increased. Further, the conjugated compound retains comparable antiviral activity to the non-derivatised nucleoside analogue of general formula (I).

According to one aspect of the present invention, therefore, there is provided a compound of the general formula (III):

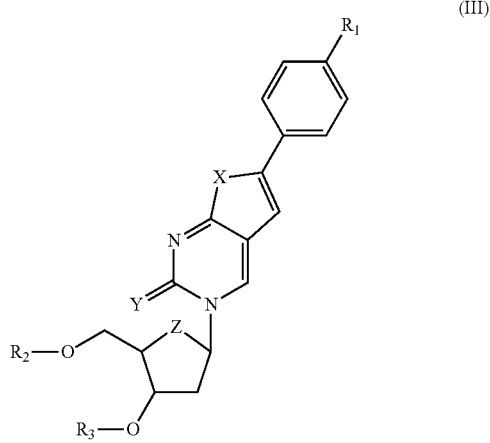

(III)

wherein X is O, S, NH or $CH_2$;
Y is O, S or NH;
Z is O, S or $CH_2$;
$R_1$ is $C_{1-8}$ alkyl, especially $C_{1-6}$ alkyl, preferably n-alkyl, e.g., n-pentyl or n-hexyl;
at least one of $R_2$ and $R_3$ is H—$[R_4—R_5]_n$—$R_6$—, in which:
  H—$[R_4—R_5]_n$— comprises an oligopeptide, $R_4$ being an amino acid and $R_5$ being an amino acid selected from proline, alanine, hydroxyproline, dihydroxyproline, thiazolidinecarboxylic acid (thioproline), dehydroproline, pipecolic acid (L-homoproline), azetidinecarboxylic acid, aziridinecarboxylic acid, glycine, serine, valine, leucine, isoleucine and threonine,
  $R_6$ is a neutral, non-polar amino acid moiety that is bonded to $R_5$ by a peptide bond, and
  n is 1, 2, 3, 4 or 5; and
the other of $R_3$ and $R_2$ is H—$[R_4—R_5]_n$—$R_6$— or H; or
a pharmaceutically acceptable salt thereof.

In some embodiments, one of $R_2$ and $R_3$ is H—$[R_4—R_5]_n$—$R_6$— and the other is H. Alternatively, both of $R_2$ and $R_3$ may be H—$[R_4—R_5]_n$—$R_6$—. Where both $R_2$ and $R_3$ are H—$[R_4—R_5]_n$—$R_6$—, $R_4$, $R_5$, $R_6$ and n are selected independently for $R_2$ and $R_3$ respectively. However, in some embodiments, $R_2$ and $R_3$ may be the same.

The compound of the present invention is cleavable by CD26. The H—$[R_4—R_5]_n$— has a free amino-terminus, i.e., an unmodified $NH_2$ group.

In some embodiments n may be 2-5, and in particular the —$[R_4—R_5]_n$— oligopeptide may be a tetrapeptide or a hexapeptide, it being understood that, in each $R_4$—$R_5$ unit, $R_4$ and $R_5$ are selected independently of the one or more other units.

Preferably, however, n=1, H—$[R_4—R_5]_n$—$R_6$ thus being a tripeptide moiety.

One or both of $R_4$ and $R_5$ may be L-amino acids, although, in some embodiments, one or both of $R_4$ and $R_5$ may be employed in their D-forms. Further, $R_4$ and $R_5$ are suitably naturally occurring amino acids.

Suitably, $R_4$ may be selected from alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine and valine.

Advantageously, $R_4$ is valine.

Suitably, $R_5$ may be selected from proline, alanine, glycine, serine, valine and leucine.

Advantageously $R_5$ is proline or alanine.

Suitably, the oligopeptide —$[R_4—R_5]$— is selected from Val-Pro, Asp-Pro, Ser-Pro, Lys-Pro, Arg-Pro, His-Pro, Phe-Pro, Ile-Pro, Leu-Pro, Val-Ala, Asp-Ala, Ser-Ala, Lys-Ala, Arg-Ala, His-Ala, Phe-Ala, Ile-Ala and Leu-Ala.

Preferably, said oligopeptide is Val-Pro.

Preferably said neutral, non-polar amino acid moiety $R_6$ is:

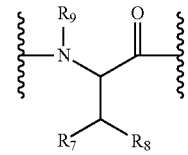

in which $R_7$, $R_8$ and $R_9$ are each independently H or $C_{1-3}$ alkyl, especially $C_{1-2}$ alkyl.

$R_9$ is preferably H.

In some embodiments, $R_6$ may be valine, leucine, isoleucine or alanine.

Preferably $R_6$ is valine. $R_6$ may be L-valine, D-valine or D,L-valine; preferably $R_6$ is L-valine.

In some preferred embodiments, $R_2$ and $R_3$ are the same, and both are H-Val-Pro-Val-.

Further, X, Y and Z are preferably all O.

Particularly preferred compounds according to the present invention are:

Compound 7

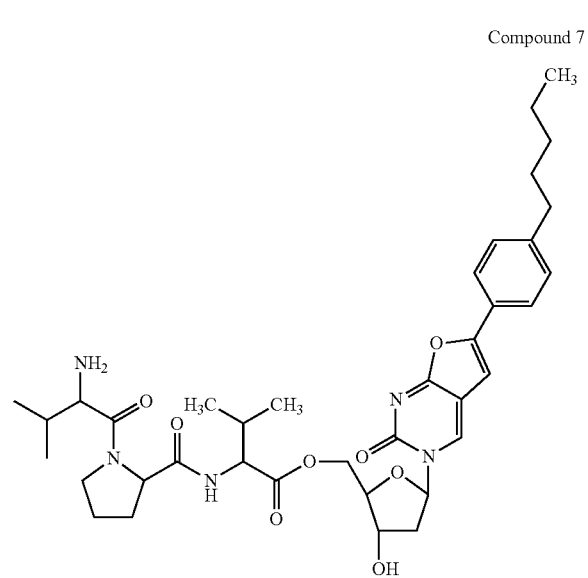

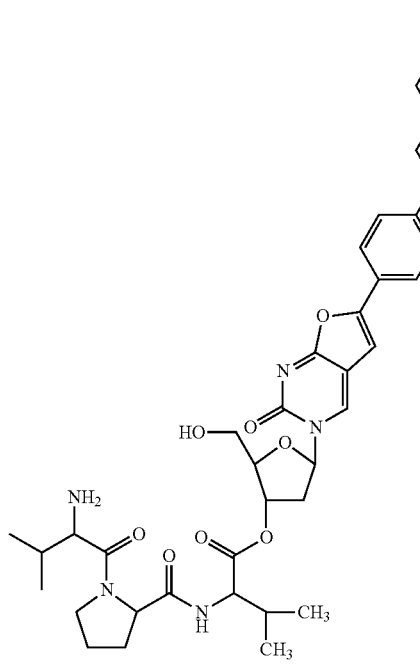

Compound 9

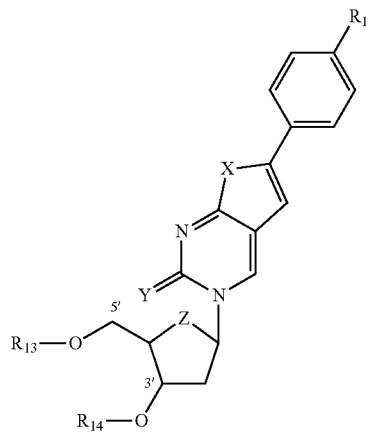

(II)

wherein X is O, S, NH or CH$_2$;
Y is O, S or NH;
Z is O, S or CH$_2$;
R$_1$ is C$_{1-6}$ alkyl, preferably n-alkyl, e.g., n-pentyl or n-hexyl;
at least one of R$_{13}$ and R$_{14}$ is a neutral, non-polar amino acid moiety having a free amino terminus; and
the other of R$_{14}$ and R$_{13}$ is H, the resulting hydroxyl group being optionally protected, or a neutral, non-polar amino acid moiety;
with a protected oligopeptide of formula Z'—[R$_4$—R$_5$]$_n$—OH to form a peptide bond between R$_5$ and at least one of R$_{13}$ or R$_{14}$, wherein R$_4$ and R$_5$ are as defined above and Z' is an amino-protecting group to protect the free amino terminus, and thereafter removing said protecting group.

Said amino-protecting group may comprise a 3. 9-fluorenylmethoxycarbonyl (Fmoc) protecting group, but other, suitable amino-protecting groups are known and available to those skilled in the art.

When R$_{13}$ is H, the resulting hydroxyl group may be protected with a suitable hydroxyl-protecting group such, for example, as tert-butyldimethylsilyl chloride. Other hydroxyl-protecting groups will be known to those skilled in the art. Once the conjugation reaction between the compound of formula (II) and the dipeptide has been completed, the hydroxyl-protecting group may be removed to expose the free 5'-OH group.

Said compound of formula (II) may be synthesised by esterifying a compound of formula (IV):

Compound 11

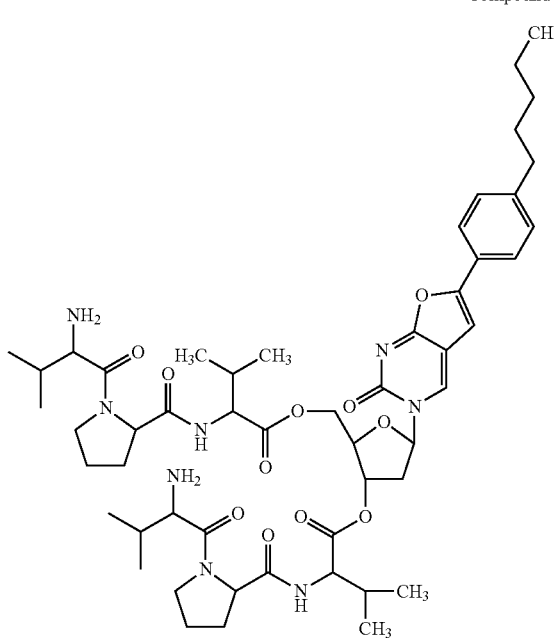

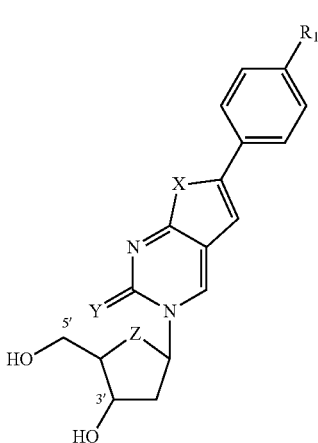

(IV)

According to another aspect of the present invention there is provided a method of synthesising the compound of the invention, said method comprising conjugating a compound of formula (II):

with a protected neutral, non-polar amino acid, wherein $R_1$, X, Y and Z are as defined above to obtain the 3'- or 5'-ester or 3',5'-diester.

In some embodiments, said amino acid may have the formula (V):

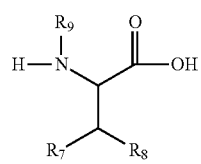

(V)

wherein $R_7$, $R_8$ and $R_9$ are as defined above.

Preferably $R_{13}$ and/or $R_{14}$ are valine, especially L-valine.

The α-amino group is suitably protected during the esterification reaction. In some embodiments, where $R_9$ is H, said amino acid may be protected using a 3. 9-fluorenylmethoxycarbonyl (Fmoc) protecting group. Other suitable protecting groups are known and available to those skilled in the art.

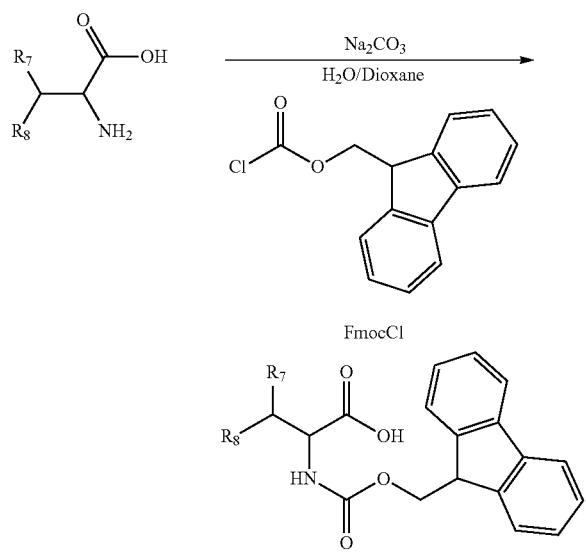

The Fmoc group may be introduced under Schotten-Baumen conditions. It is exceptionally stable towards acid. The cleavage of this group may be base catalysed (ammonia, piperidine, morpholine, DBU) undergoing an E1 β-elimination mechanism.

The esterification reaction conditions may be suitably adjusted as desired to obtain the 3'- or 5'-ester or the 3',5'-diester. Where the 3'-(mono) ester is desired, the 5'-OH group may be protected as described above using a suitable hydroxyl-protecting group such, for example, as tert-butyldimethylsilyl chloride, which may be removed after completion of the esterification reaction or left in situ for the subsequent conjugation reaction with the protected oligopeptide.

The 5'-esterification is preferably carried out under Mitsunobu conditions[1]:

[1] Mitsunobu, Synthesis, January 1981: 1-28

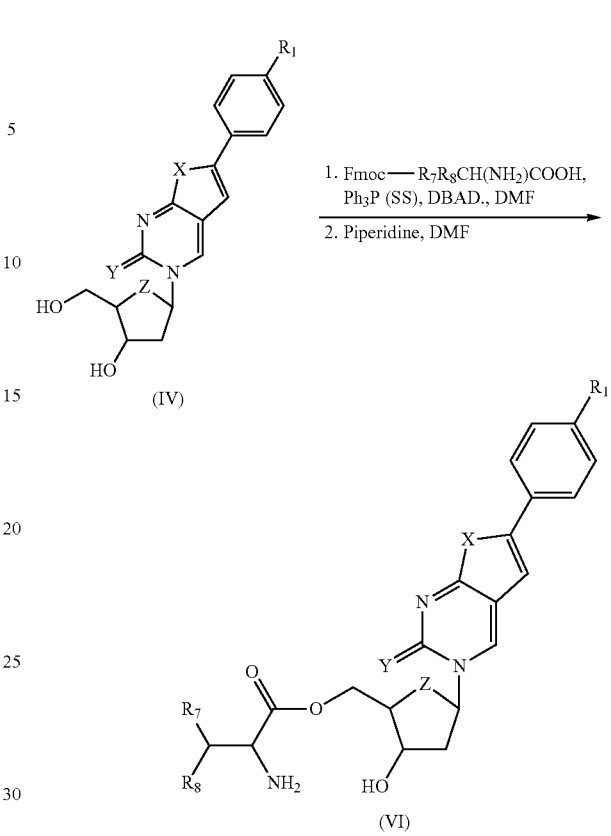

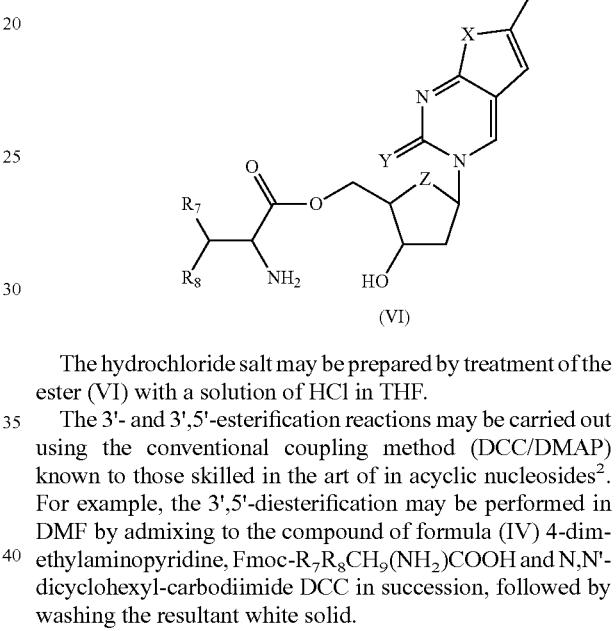

The hydrochloride salt may be prepared by treatment of the ester (VI) with a solution of HCl in THF.

The 3'- and 3',5'-esterification reactions may be carried out using the conventional coupling method (DCC/DMAP) known to those skilled in the art of in acyclic nucleosides[2]. For example, the 3',5'-diesterification may be performed in DMF by admixing to the compound of formula (IV) 4-dimethylaminopyridine, Fmoc-$R_7R_8CH_9(NH_2)COOH$ and N,N'-dicyclohexyl-carbodiimide DCC in succession, followed by washing the resultant white solid.

[2] See, e.g., "Amino acid ester prodrugs of acyclovir," Antiviral Chemistry & Chemotherapy, 1992; 3: 157-164

3'-esterification may be performed in a similar manner by reacting the 5'-protected hydroxyl compound of formula (IV) dissolved in DMF with 4-dimethylaminopyridine, Fmoc-$R_7R_8CH_9(NH_2)COOH$ and N,N' dicyclohexyl-carbodiimide DCC in succession.

Preferably, $R_1$ is n-pentyl, X, Y and Z are all O, and $R_7$ and $R_8$ are both methyl.

It has been found that the compound of the present invention has advantageous pharmacokinetic (PK) properties and improved bioavailability as compared to Compound 1 of WO 01/83501 A1. The conjugation of a dipeptide moiety to the free amino terminus of the valyl ester of PCT/GB2007/001677 appears not to impair the bioavailability of the compound. Further, it has been found that the compound of the invention exhibits unexpectedly high solubility in water as compared with Compound 1.

Bioavailability is often a key factor in the practical application of a drug as a therapeutic agent and compounds that demonstrate enhanced PK and/or solubility generally have improved potency in vivo over compounds with less favorable PK properties even though their in vitro potency may be similar. Such compounds, i.e., derivatives of known in vitro active compounds, are often referred to as prodrugs. Novel Compound 7 is an example of such a prodrug.

Compounds 7 and 9 were tested for antiviral activity as described below and found to be active. In addition, a comparative study of the pharmacokinetic behaviour of Compounds 1, 5 and 7 was conducted in a mouse model, demonstrating the improved bioavailability of Compounds 5 and 7 as compared to Compound 1.

Surprisingly, the water-solubility of Compound 7 was found to be more than 57-fold greater than the water-solubility of Compound 1.

For therapeutic use, a pharmaceutically acceptable salt of the compound of the invention may comprise a counter-ion that is pharmaceutically physiologically acceptable. The pharmaceutically or physiologically acceptable acid addition salt forms that the compound of the invention is able to form can conveniently be prepared using the appropriate acids such, for example, as inorganic acids such as hydrohalic acids, e.g., hydrochloride or hydrobromic acid, sulfuric, nitric, phosphoric and the like acids; or organic acids such, for example, as acetic, propanoic, hydroxyacetic, lactic, pyruvic, oxalic, malonic, succinic, maleic, fumaric, malic, tartaric, citric, methanesulfuric, ethanesulfuric, benzenesulfonic, p-toluenesulfonic, cyclamic, salicylic, p-amino-salicylic, pamoic and the like acids.

Conversely, said acid addition salt forms can be converted by treatment with an appropriate base into the free base form.

The compound of the invention containing an acidic proton may also be converted into its non-toxic metal or amine addition salt by treatment with appropriate organic and inorganic bases. Appropriate base salt forms comprise, for example, the ammonium salts, quaternary ammonium salts, the alkali and earth alkaline metal salts, e.g., the lithium, sodium, potassium, magnesium, calcium salts and the like, salts with organic bases, e.g., the benzathine, N-methyl, -D-glucamine, hydrabamine salts and bases, and salts with amino acids, such as, for example, arginine, lysine and the like.

Conversely, said base addition forms can be converted by treatment with an appropriate acid into the free acid form.

The term "salt" as used herein also comprises the hydrate and solvent addition forms that the compound of the invention is able to form. Examples of such forms are, e.g., hydrates, alcoholate and the like. The term "salt" also comprehends the quaternisation of the nitrogen atoms of the compound. A basic nitrogen can be quaternised with any agent known to those skilled in the art including, for instance, lower alkyl halides, dialkyl sulfates, long chain halides and arylalkyl halides.

The compound of the invention may also exist in its tautomeric forms. Such forms, although not explicitly indicated in the above formula (III), are intended to be included within the scope of the present invention.

According to another aspect of the present invention therefore there is provided a compound according to the present invention for use in a method of treatment, particularly the prophylaxis or treatment of a viral infection. In some embodiments, said compound may be provided for use in the treatment or prophylaxis of an infection with the Varicella Zoster virus.

According to a yet another aspect of the present invention there is provided use of a compound according to the present invention in the manufacture of a medicament for the prophylaxis or treatment of viral infection, especially a viral infection caused by the Varicella Zoster virus, e.g., chicken pox or shingles.

According to yet another aspect of the present invention there is provided a method of prophylaxis or treatment of viral infection, said method comprising administration to a human or non-human animal patient in need of such treatment an effective amount of a compound according to the present invention.

According to a further aspect of the present invention there is provided a pharmaceutical composition comprising a compound of the present invention in combination with a pharmaceutically acceptable excipient.

Medicaments embodying the present invention can be administered by oral, enteral or parenteral routes, including intravenous, intramuscular, intraperitoneal, subcutaneous, transdermal, airway (aerosol), rectal, vaginal and topical (including buccal and sublingual) administration.

For oral administration, compounds embodying the present invention will generally be provided in the form of tablets or capsules, as a powder or granules, or as an aqueous solution or suspension.

Tablets for oral use may include the active ingredient mixed with pharmaceutically acceptable excipients such as inert diluents, disintegrating agents, binding agents, lubricating agents, sweetening agents, flavouring agents, colouring agents and preservatives. Suitable inert diluents include sodium and calcium carbonate, sodium and calcium phosphate, and lactose, while corn starch and alginic acid are suitable disintegrating agents. Binding agents may include starch and gelatin, while the lubricating agent, if present, will generally be magnesium stearate, stearic acid or talc. If desired, the tablets may be coated with a material such as glyceryl monostearate or glyceryl distearate, to delay absorption in the gastrointestinal tract.

Capsules for oral use include hard gelatin capsules in which the active ingredient is mixed with a solid diluent, and soft gelatin capsules wherein the active ingredient is mixed with water or an oil such as peanut oil, liquid paraffin or olive oil.

Formulations for rectal administration may be presented as a suppository with a suitable base comprising for example cocoa butter or a salicylate.

Formulations suitable for vaginal administration may be presented as pessaries, tampons, creams, gels, pastes, foams or spray formulations containing in addition to the active ingredient such carriers as are known in the art to be appropriate.

For intramuscular, intraperitoneal, subcutaneous and intravenous use, compounds embodying the present invention will generally be provided in sterile aqueous solutions or suspensions, buffered to an appropriate pH and isotonicity. Suitable aqueous vehicles include Ringer's solution and isotonic sodium chloride. Aqueous suspensions embodying the invention may include suspending agents such as cellulose derivatives, sodium alginate, polyvinyl-pyrrolidone and gum tragacanth, and a wetting agent such as lecithin. Suitable preservatives for aqueous suspensions include ethyl and n-propyl p-hydroxybenzoate.

Compounds embodying the present invention can be presented as liposome formulations.

In general, a suitable dose will be in the range of 0.001 to 300 mg per kilogram body weight of the recipient per day, preferably in the range of 0.01 to 25 mg per kilogram body weight per day, and most preferably in the range 0.05 to 10 mg per kilogram body weight per day. The desired dose may be presented as two, three, four, five or six or more sub-doses administered at appropriate intervals throughout the day. These sub-doses may be administered in unit dosage forms, for example, containing 0.1 to 1500 mg, preferably 0.2 to 1000 mg, and most preferably 0.5 to 700 mg of active ingredient per unit dosage form.

In a particularly preferred embodiment, a dose of 100-500 mg of the compound of the present invention may be administered once per day.

Following is a description by way of example only with reference to the accompanying drawings of embodiments of the present invention.

DESCRIPTION 1

Figure 1:
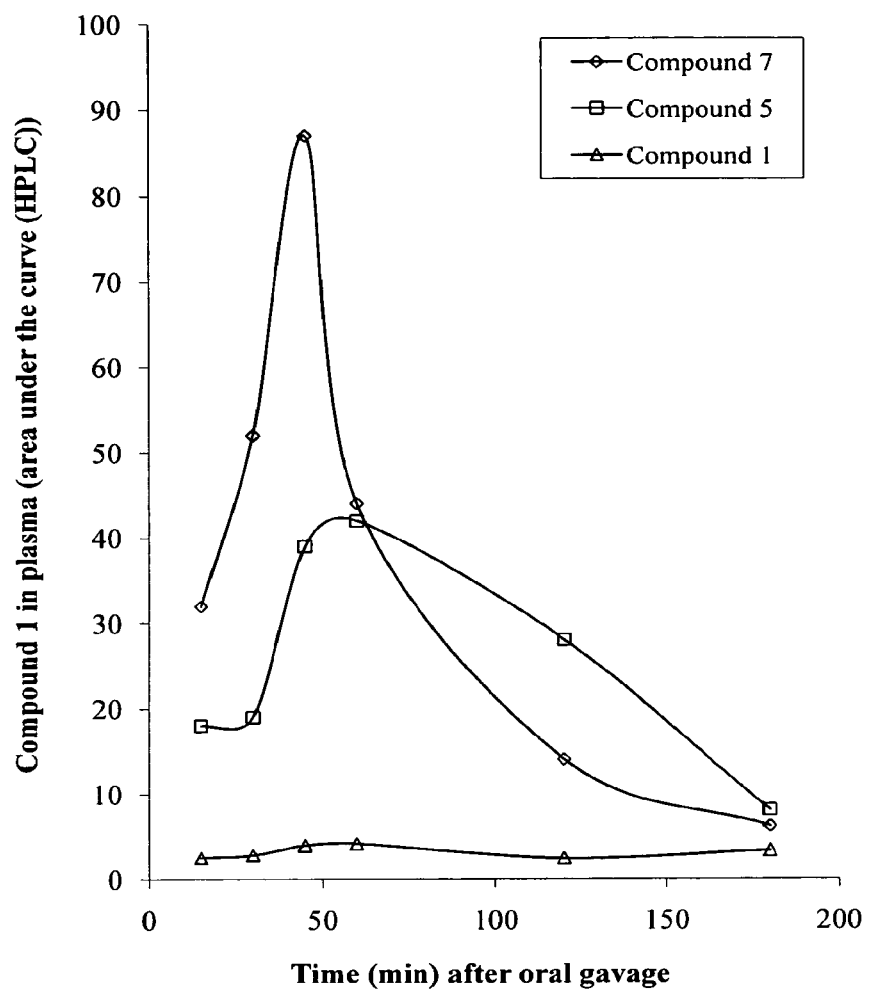
FIG. 1 is a graph showing the bioavailability (in arbitrary units) of Compounds 1, 5 and 7 at certain times after oral gavage.

Preparation of Compound 5; Formation of Valine Ester

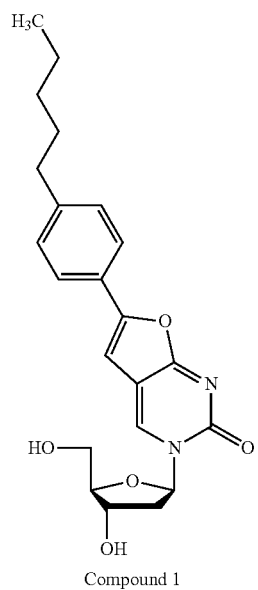

Compound 1

Compound 1 (200 mg, 0.5 mmol, prepared as described in WO 01/83501 A1, Example 3, page 15) was dissolved in dry DMF (5 mL), followed by the addition of polymer-bound triphenylphosphine [370 mg, 1.1 mmol, (3 mmol p/g resin)] and di-tert-butyl azodicarboxylate (DBAD) (231 mg, 1.0 mmol) to the mixture and stirred for 20 minutes. A solution of Fmoc-Val-OH (340 mg, 1.0 mmol) in DMF (5 mL) was added dropwise over a period of 30 minutes. The reaction mixture was stirred at room temperature under an argon atmosphere until complete disappearance of the starting material (overnight). The resin was filtered off and washed with ethyl acetate. Piperidine (1 mL, 10 mmol) was added to the solution and stirred for 10 minutes. The solvent was removed under reduced pressure without warming over 35° C. and the residue was dissolved in ethyl acetate (20 mL), washed with 10% $NaHCO_3$ (3×20 mL) and brine (2×20 mL). The final residue was purified by column chromatography (gradient $CH_2Cl_2$: MeOH 100% 98% 95% 90%), to give 137 mg of Compound 5 (55% yield) as a yellow solid.

$^1$H-NMR ($CDCl_3$) δ: 8.3 (1H, s), 7.55 (2H, d), 7.15 (2H, d), 6.6 (1H, s), 6.25 (1H, t), 4.45-4.30 (4H, m), 3.23 (1H, d), 2.80 (1H, m), 2.53 (2H, t), 2.12 (1H, m), 1.97 (1H, m), 1.60 (2H, m), 1.24 (4H, m), 0.90-0.78 (9H, m).

$^{13}$C-NMR ($CDCl_3$) δ: 175.16, 171.62, 156.26, 154.89, 145.19, 135.29, 129.02, 125.69, 124.95, 108.60, 96.82, 88.73, 85.08, 70.90, 64.19, 60.19, 41.91, 35.82, 32.32, 31.44, 30.89, 22.50, 19.30, 17.24, 13.99.

Example 1

Preparation of Fmoc-Compound 7; Formation of Fmoc-Val-Pro-Val Conjugate (3-[2'-Deoxy-5'-O-[N-(fluorenilmethoxycarbonyl)-valyl-prolyl-valyl]-β-D-ribofuranosyl]-6-(p-pentylphenyl)-2,3-dihydrofuro[2,3-d]pyrimidine-2-one)

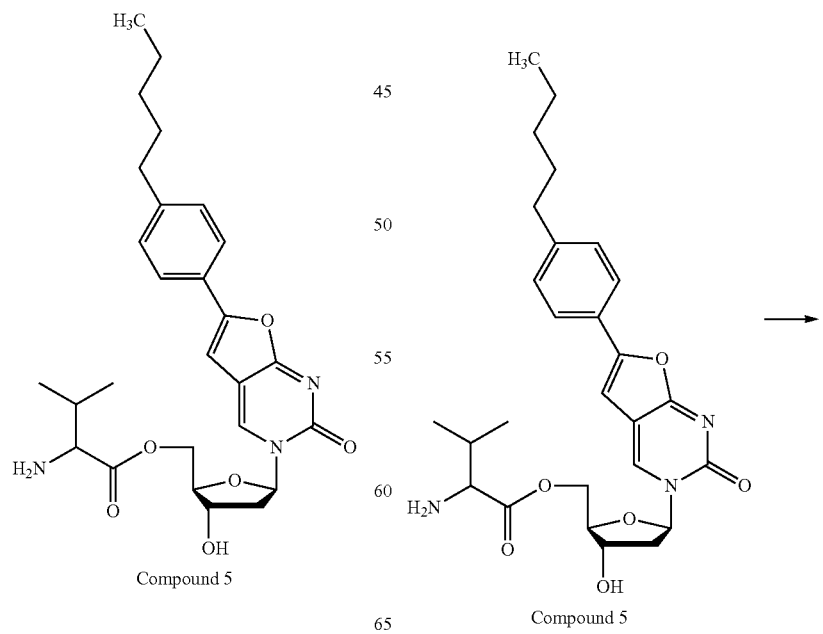

Compound 5

Compound 5

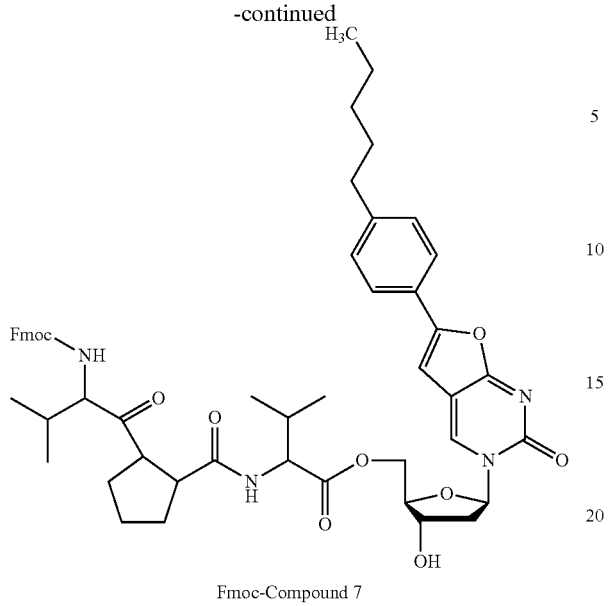

Fmoc-Compound 7

A solution of Compound 5 prepared as described above in Description 1 (95 mg, 0.19 mmol) in dichloromethane (5 mL) was successively treated with the commercially available amino-protected dipeptide Fmoc-Val-Pro-OH (100 mg, 0.23 mmol), (benzotriazol-1-yl-oxy)-tris-(dimethylamino)-phosphonium hexafluorophosphate (BOP) (101 mg, 0.23 mmol) and triethylamine (0.032 mL, 0.23 mmol). The reaction mixture was stirred at room temperature for 15 hours and the solvent was evaporated to dryness. The residue was dissolved in ethyl acetate 26 (50 mL), washed with 10% aqueous citric acid (3×20 mL), 10% aqueous NaHCO$_3$ (3×20 mL), water (3×20 mL) and brine (3×20 mL). The organic layer was dried (Na$_2$SO$_4$), filtered and evaporated to dryness. The final residue was purified by CCTLC on the Chromatotron (dichloromethane-methanol, 25:1) to give the protected derivative Fmoc-Compound 7 (130 mg, 74%) as a white amorphous solid.

$^1$H NMR (300 MHz, acetone-d$_6$) δ: 0.84-1.04 (m, 15H, 2γ-CH$_3$, Val$_1$ y Val$_2$, CH$_3$), 1.20-1.41 (m, 4H, CH$_2$), 1.62 (m, 2H, CH$_2$), 1.91-2.18 (m, 6H, β-CH, Val$_1$ y Val$_2$, β-CH$_2$, Pro, γ-CH$_2$, Pro), 2.37 (m, 1H, H-2'a), 2.62-2.70 (m, 3H, H-2'b, CH$_2$), 3.69-3.84 (m, 2H, δ-CH$_2$, Pro), 4.22-4.72 (m, 11H, CH$_2$, Fmoc, CH, Fmoc, 2H-5', H-4', H-3', 2α-CH, Val$_1$ y Val$_2$, α-CH, Pro, OH), 6.30 (t, 1H, H-1', J=5.9 Hz), 6.44 (d, 1H, NH, Val$_1$, J=8.5 Hz), 7.22 (s, 1H, H-5), 7.35 y 7.81 (AA'BB' system, 4H, Ar, J=8.5 Hz), 7.30-7.89 (m, 9H, Ar, Fmoc, NH, Val$_2$), 8.73 (s, 1H, H-4).

$^{13}$C NMR (100 MHz, acetone-d$_6$) δ; 13.6 (CH$_3$), 17.7, 18.1, 18.7, 19.1 (4C-γ, Val$_1$ y Val$_2$), 22.5, 25.1, 28.4, 30.8, 31.1, 31.2 (4CH$_2$, C-β, Pro, C-γ, Pro), 31.5, 35.7 (2C-β, Val$_1$ y Val$_2$), 41.8 (C-2'), 47.4, 47.7 (C-δ, Pro, CH Fmoc), 58.1, 58.6 (C-α, Val$_2$, C-α, Pro), 59.9 (C-α, Val$_1$), 64.1 (C-5'), 66.6 (CH$_2$, Fmoc), 70.5 (C-3'), 85.3, 88.5 (C-1', C-4'), 99.0 (C-5), 107.7 (C-4a), 120.1, 125.0, 125.1, 125.6, 127.3, 127.9 (4C—Ar, Fmoc, C-Hb, ipso-C), 129.2 (C-Ha), 137.1 (C-4), 141.4 (C—Ar, Fmoc), 144.4, 144.6 (para-C, C—Ar, Fmoc), 154.3, 154.7 (C-6, C=O, Fmoc), 156.5 (C-2), 171.1, 171.7, 172.0, 172.1 (C=O, Val$_1$, C=O, Val$_2$, C=O, Pro, C-7a).

MS (ESI$^+$): m/z 916.3 (M+1)$^+$, 938.0 (M+Na)$^+$. Elemental analysis calcd (%) for C$_{52}$H$_{61}$N$_5$O$_{10}$: C, 68.18; H, 6.71; N, 7.65. found: C, 68.01; H, 6.95; N, 7.79.

Example 2

Preparation of Compound 7; Deprotection of the Fmoc-Val-Pro-Val Conjugate

3-[2'-Deoxy-5'-O-(valyl-prolyl-valyl)-β-D-ribofuranosyl]-6-(p-pentylphenyl)-2,3-dihydrofuro[2,3-d]pyrimidine-2-one)

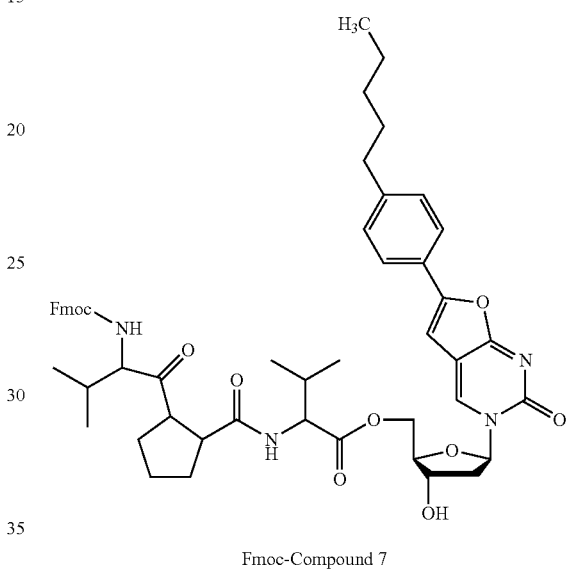

Fmoc-Compound 7

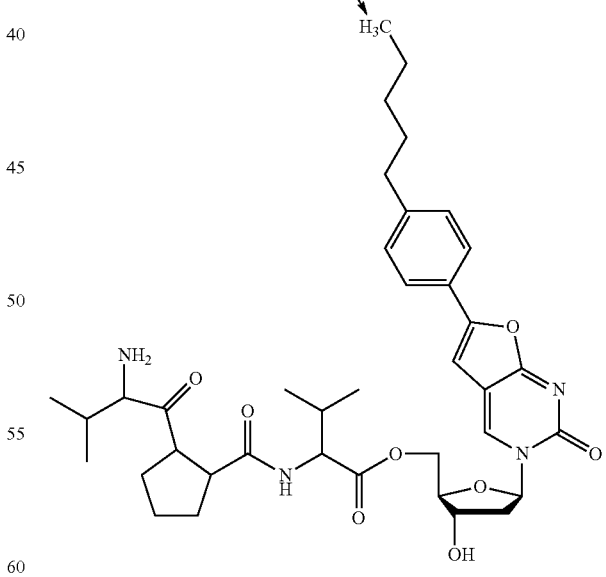

Compound 7

To a solution of Fmoc-Compound 7 prepared as described in Example 1 above (120 mg, 0.13 mmol) in DMF (3 ml) piperidine (0.15 ml, 1.5 mmol) was added and the mixture was stirred for 10 minute. The solvent was removed under reduced pressure and the residue was purified by CCTLC on the Chromatotron (ethyl acetate-methanol, 10:1) to give the deprotected derivative Compound 7 (81 mg, 89%) as a white foam.

$^1$H NMR (300 MHz, acetone-$d_6$) δ: 0.78-0.97 (m, 15H, 2γ-CH$_3$, Val$_1$ y Val$_2$, CH$_3$), 1.17-1.41 (m, 4H, CH$_2$), 1.65 (m, 2H, CH$_2$), 1.83-2.35 (m, 7H, 2β-CH, Val$_1$ y Val$_2$, β-CH$_2$, Pro, γ-CH$_2$, Pro, H-2'a), 2.59-2.70 (m, 3H, H-2'b, CH$_2$), 3.51-3.78 (m, 2H, δ-CH$_2$, Pro), 3.93 (d, 1H, α-CH, Val$_1$, J=8.1 Hz), 4.32-4.58 (m, 7H, 2H-5', H-4', H-3', α-CH, Val$_2$, α-CH, Pro, OH), 6.31 (t, 1H, H-1', J=5.8 Hz), 7.25 (s, 1H, H-5), 7.33 (AA'BB' system, 2H, Ar, J=8.5 Hz), 7.75-7.86 (m, 3H, Ar, NH, Val$_2$), 8.71 (s, 1H, H-4).

$^{13}$C NMR (100 MHz, acetone-$d_6$) δ; 13.9 (CH$_3$), 18.4, 19.0, 19.1, 19.6 (4C-γ, Val$_1$ y Val$_2$), 22.8, 25.4, 28.2, 31.0, 31.4, 31.8 (4CH$_2$, C-β, Pro, C-γ, Pro), 32.5, 35.9 (2C-β, Val$_1$ y Val$_2$), 42.0 (C-2'), 47.6 (C-δ, Pro), 58.8 (C-α, Val$_2$), 60.1, 60.4 (C-α, Val$_1$, C-α, Pro), 64.4 (C-5'), 70.8 (C-3'), 85.6, 88.8 (C-1', C-4'), 99.4 (C-5), 108.2 (C-4a), 125.3 (C-Hb), 127.1 (ipso-C), 129.5 (C-Ha), 137.5 (C-4), 144.9 (para-C), 154.8 (C-6), 155.1 (C-2), 168.9, 172.0, 172.3, 172.7 (C=O, Val$_1$, C=O, Val$_2$, C=O, Pro, C-7a).

MS (ESI$^+$): m/z 694.3 (M+1)$^+$, 716.5 (M+Na)$^+$, 1387.7 (2M+1)$^+$, 1409.6 (2M+Na)$^+$. Elemental analysis calcd. (%) for $C_{37}H_{53}N_5O_7$: C, 65.37; H, 7.86; N, 10.30. found: C, 65.26; H, 8.01; N, 10.49.

Example 3

Preparation of Fmoc-Compound 8; Formation of 3'-Valine Ester

3-[2'-Deoxy-3'-O-[N-(fluorenilmethoxycarbonyl)-valyl]-5'-O-(tert-butyldimethylsilyl)-β-D-ribofurano-syl]-6-(p-pentylphenyl)-2,3-dihydrofuro[2,3-d]pyrimidin-2-one

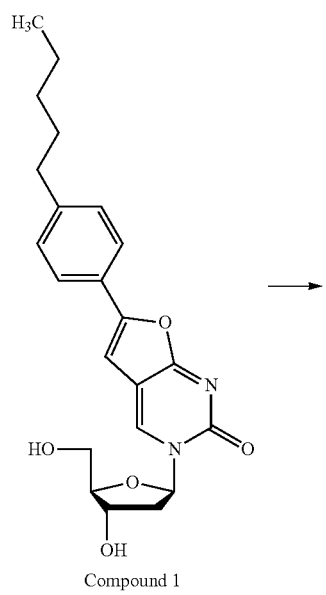

Compound 1

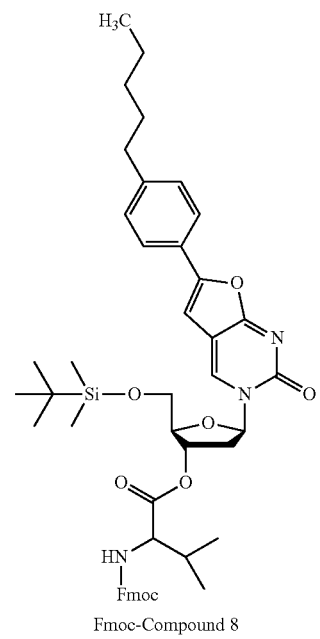

Fmoc-Compound 8

To a solution of Compound 1 (200 mg, 0.5 mmol) in dry pyridine (4 ml), tert-butyldimethylsilyl chloride (302 mg, 2.0 mmol) was added. The reaction mixture was stirred at room temperature under an argon atmosphere for 48 hours. The solvent was removed under reduced pressure. The residue (5'-silyl derivative) was dissolved in DMF (3 ml) and 4-dimethylaminopyridine (12 mg, 0.1 mmol), Fmoc-Val-OH (225 mg, 0.66 mmol) and N,N'-dicyclohexyl-carbodiimide (137 mg, 0.66 mmol) were successively added at 0° C. The reaction mixture was stirred at room temperature for 2 hours. The white solid was filtered, washed with DMF and the solvent was evaporated to dryness. The residue, thus obtained, was dissolved in ethyl acetate (50 mL), washed with 10% aqueous citric acid (3×20 mL), 10% aqueous NaHCO$_3$ (3×20 mL), water (3×20 mL) and brine (3×20 mL). The organic layer was dried (Na$_2$SO$_4$), filtered and evaporated to dryness. The final residue was purified by flash column chromatography on silica gel (dichloromethane/methanol, 40:1) to give 230 mg (83%) of Fmoc-Compound 8 as a white foam.

$^1$H NMR (300 MHz, acetone-$d_6$): δ 0.14 (s, 3H, CH$_3$, Si—CH$_3$), 0.16 (s, 3H, CH$_3$, Si—CH$_3$), 0.89 (m, 12H, $^t$Bu, CH$_3$), 1.02 (d, 6H, γ-CH$_3$, Val), 1.27-1.40 (m, 4H, 2CH$_2$), 1.63 (m, 2H, CH$_2$), 1.81 (m, 1H, β-CH, Val), 2.21-2.39 (m, 2H, 2H-2'), 2.66 (t, 2H, CH$_2$, J=7.3 Hz), 4.02 (m, 2H, 2H-5'), 4.17-4.40 (m, 5H, CH$_2$, Fmoc, CH, Fmoc, H-4', α-CH, Val), 5.40 (m, 1H, H-3'), 6.31 (t, 1H, H-1', J=5.9 Hz), 6.98 (d, 1H, NH, J=8.8 Hz), 7.03 (s, 1H, H-5), 7.29-7.86 (m, 8H, Ar Fmoc), 7.33 y 7.74 (AA'BB' system, 4H, Ar, J=8.1 Hz), 8.68 (s, 1H, H-4).

MS (ESI+): m/z 834.3 (M+1$^+$).

Elemental analysis: calcd (%) for $C_{48}H_{61}N_3O_8Si$: C, 68.95; H, 7.35; N, 5.03. found: C, 69.07; H, 7.49; N, 5.58.

Example 4

Fmoc-Deprotection of Compound 8

3-[2'-Deoxy-3'-O-valyl-5'-O-(tert-butyldimethylsilyl)-β-D-ribofuranosyl]-6-(p-pentylphenyl)-2,3-dihydrofuro[2,3-d]pyrimidin-2-one

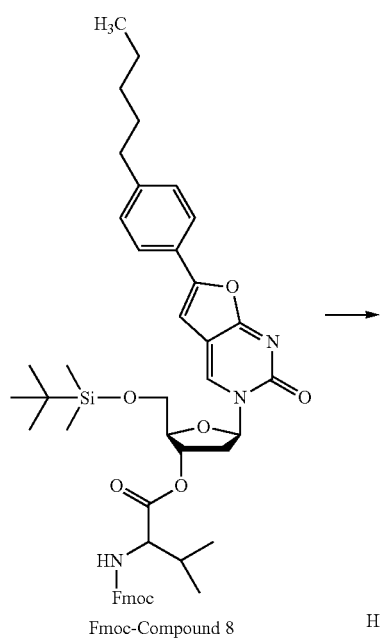

Fmoc-Compound 8

↓

Compound 8

To a solution of Fmoc-Compound 8 (179 mg, 0.22 mmol) in DMF (5 ml), piperidine (0.25 ml, 2.5 mmol) was added and the mixture was stirred for 5 minutes. The solvent was evaporated to dryness. The residue was purified by CCTLC on the Chromatotron (dichloromethane/methanol, 20:1) to afford 122 mg (93%) of Compound 8 as a yellow foam.

$^1$H NMR (300 MHz, acetone-$d_6$): δ 0.16 (s, 3H, $CH_3$, Si—$CH_3$), 0.18 (s, 3H, $CH_3$, Si—$CH_3$), 0.87-0.99 (m, 18H, $^tBu$, γ-$CH_3$, Val, $CH_3$), 1.29-1.40 (m, 4H, 2$CH_2$), 1.66 (m, 2H, $CH_2$), 2.03 (m, 1H, β-CH, Val), 2.22-2.37 (m, 2H, 2H-2'), 2.67 (t, 2H, $CH_2$, J=7.5 Hz), 3.92 (d, 1H, α-CH, Val, J=6.8 Hz), 4.05 (m, 2H, 2H-5'), 4.33 (m, 1H, H-4'), 5.37 (m, 1H, H-3'), 6.29 (m, 1H, H-1'), 7.03 (s, 1H, H-5), 7.34 y 7.75 (AA'BB' system, 4H, Ar, J=8.1 Hz), 8.70 (s, 1H, H-4).

MS (ESI+): m/z 612.4 (M+1$^+$).

Elemental analysis: calcd (%) for $C_{33}H_{51}N_3O_6Si$: C, 64.57; H, 8.37; N, 6.85. found: C, 64.44; H, 8.51; N, 6.89.

Example 5

Preparation of Fmoc-Compound 9; Formation of 3'-Fmoc-Val-Pro-Val Conjugate

3-[2'-Deoxy-3'-O-[N-(fluorenilmethoxycarbonyl)-valyl-prolyl-valyl]-5'-O-(tert-butyldimethylsilyl)-β-D-ribofuranosyl]-6-(p-pentylphenyl)-2,3-dihydrofuro[2,3-d]pyrimidin-2-one

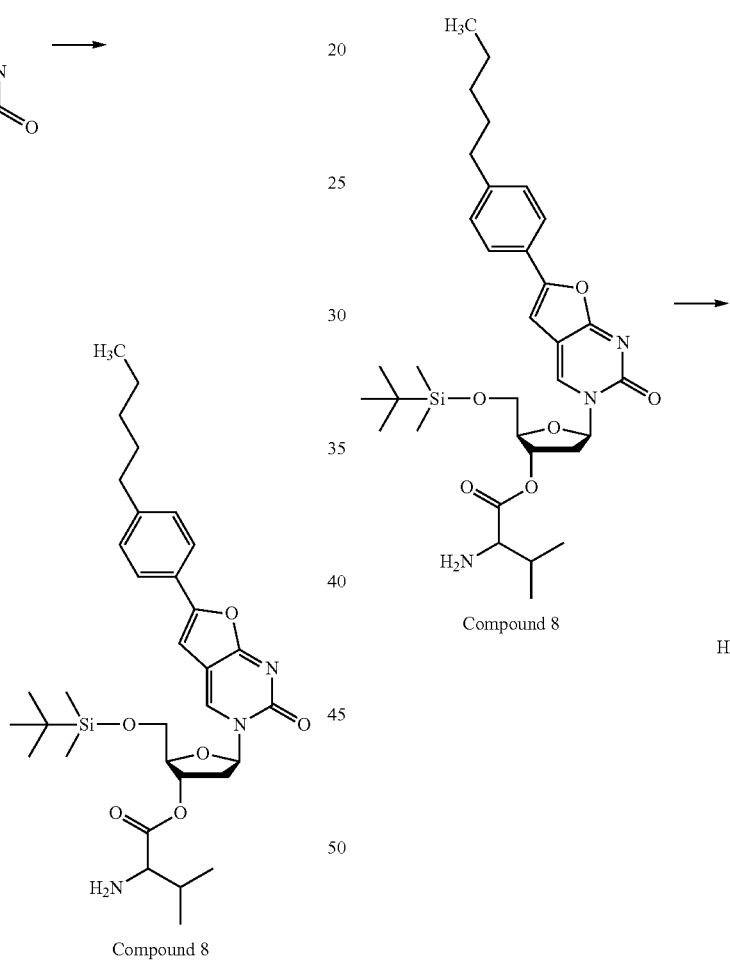

Compound 8

↓

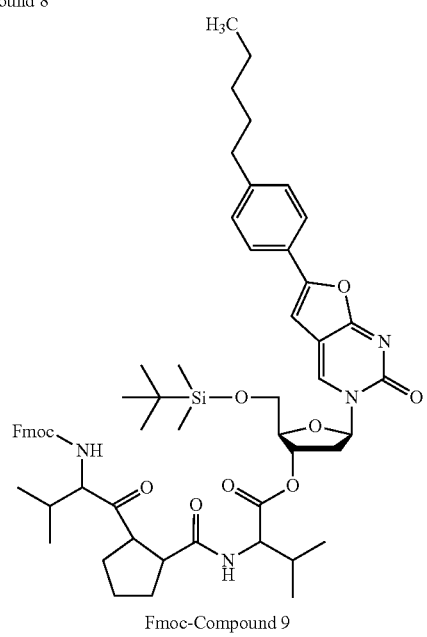

Fmoc-Compound 9

Following the method described in Example 1 for the synthesis of Fmoc-compound 7, a solution of Compound 8 (81 mg, 0.13 mmol) in dichloromethane (2 ml) was successively reacted with Fmoc-Val-Pro-OH (69 mg, 0.16 mmol), BOP (70 mg, 0.16 mmol) and triethylamine (0.022 ml, 0.16 mmol) for 15 hours. After the work-up the final residue was by CCTLC on the Chromatotron (dichloromethane/methanol, 50:1) to afford 109 mg (80%) of Fmoc-Compound 9 as a white foam.

$^1$H NMR (300 MHz, acetone-$d_6$): δ 0.16 (s, 3H, $CH_3$, Si—$CH_3$), 0.18 (s, 3H, $CH_3$, Si—$CH_3$), 0.86-1.05 (m, 24H, $^t$Bu, 2γ-$CH_3$, $Val_1$, $Val_2$, $CH_3$), 1.30-1.36 (m, 4H, $2CH_2$), 1.64 (m, 2H, $CH_2$), 1.96-2.38 (m, 8H, 2β-CH, $Val_1$, $Val_2$, β-$CH_2$, Pro, γ-$CH_2$, Pro, 2H-2'), 2.66 (t, 2H, $CH_2$, J=7.3 Hz), 3.63-3.82 (m, 2H, δ-$CH_2$, Pro), 4.06 (m, 2H, 2H-5'), 4.21-4.38 (m, 6H, $CH_2$, Fmoc, CH, Fmoc, 2α-CH $Val_1$, $Val_2$, α-CH, Pro), 4.61 (m, 1H, H-4'), 5.40 (m, 1H, H-3'), 6.45 (m, 1H, H-1'), 6.66 (d, 1H, NH, $Val_1$, J=8.3 Hz), 7.03 (s, 1H, H-5), 7.28-7.86 (m, 9H, Ar, Fmoc, NH $Val_2$), 7.34 y 7.75 (AA'BB' system, 4H, Ar, J=8.1 Hz), 8.71 (s, 1H, H-4).

MS (ESI+): m/z 1030.3 (M+1$^+$).

Elemental analysis: calcd (%) for $C_{58}H_{77}N_5O_{10}Si$: C, 67.48; H, 7.52; N, 6.78. found: C, 67.63; H, 7.59; N, 6.81.

Example 6

Full Deprotection of Fmoc-Compound 9

3-[2'-Deoxy-3'-O-(valyl-prolyl-valyl)-β-D-ribofuranosyl]-6-(p-pentylphenyl)-2,3-dihydrofuro[2,3-d]pyrimidin-2-one

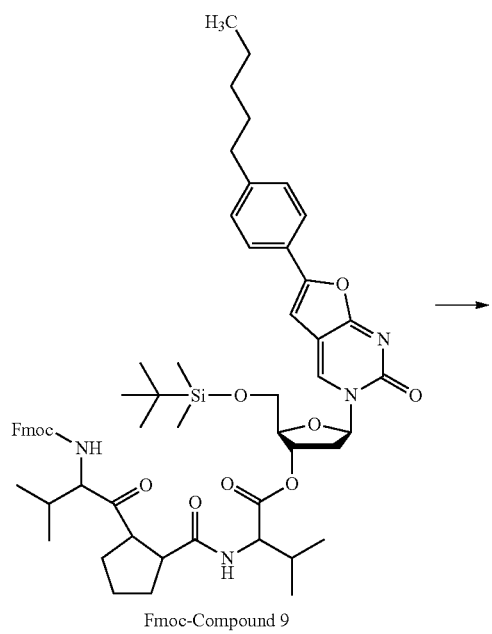

Fmoc-Compound 9

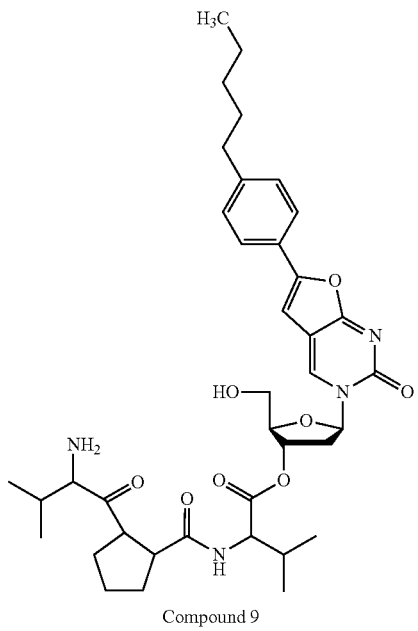

Compound 9

According to the deprotection method described for Compound 3 (See Example 7 below), a solution of Fmoc-Compound 9 (109 mg, 0.11 mmol) in MeOH (2 ml) was reacted with HCl 0.1N in MeOH (1.1 ml, 0.11 mmol) for 3 hours. The residue obtained after the work-up, was dissolved in DMF (2 mL) and piperidine was added. After 5 minutes at room temperature the solvent was evaporated to dryness. The final residue was purified by CCTLC on the Chromatotron (dichloromethane/methanol, 50:1) to afford 40 mg (52%) of the fully deprotected Compound 9 as a yellow foam.

$^1$H NMR (300 MHz, acetone-$d_6$): δ 0.83-1.02 (m, 15H, 2γ-$CH_3$, $Val_1$, $Val_2$, $CH_3$), 1.29-1.39 (m, 4H, $2CH_2$), 1.65 (m, 2H, $CH_2$), 1.88-2.48 (m, 8H, 2β-CH, $Val_1$, $Val_2$, β-$CH_2$, Pro, γ-$CH_2$, Pro, 2H-2'), 2.66 (t, 2H, $CH_2$, J=7.5 Hz), 3.53-3.76 (m, 3H, α-CH, $Val_1$, δ-$CH_2$, Pro), 3.93-4.55 (m, 6H, 2H-5', H-4', α-CH $Val_2$, α-CH, Pro, OH), 5.43 (m, 1H, H-3'), 6.37 (m, 1H, H-1'), 7.05 (s, 1H, H-5), 7.34 y 7.74 (AA'BB' system, 4H, Ar, J=8.5 Hz), 7.69 (d, 1H, NH, $Val_2$, J=7.9 Hz), 8.86 (s, 1H, H-4).

MS (ESI+): m/z 694.3 (M+1$^+$).

Elemental analysis: calcd (%) for $C_{37}H_{53}N_5O_8$: C, 63.86; H, 7.68; N, 10.06. found: C, 64.01; H, 7.54; N, 10.21.

Example 7

Silyl and Fmoc Deprotection of Fmoc-Compound 8

3-[2'-Deoxy-3'-O-valyl-β-D-ribofuranosyl]-6-(p-pentylphenyl)-2,3-dihydrofuro[2,3-d]pyrimidin-2-one If desired, Fmoc-Compound 8 may be fully deprotected to form Compound 3 of PCT/GB2007/00167.

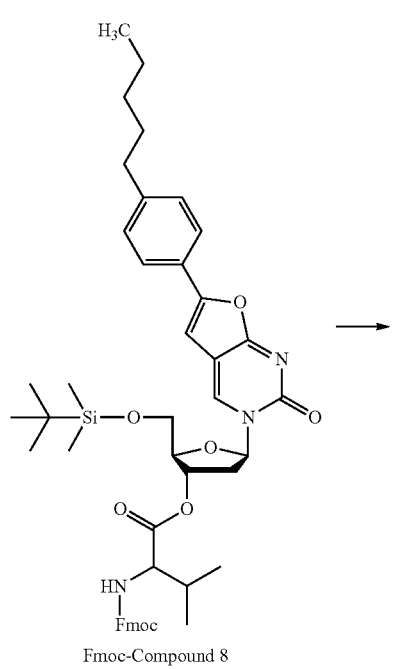

Fmoc-Compound 8

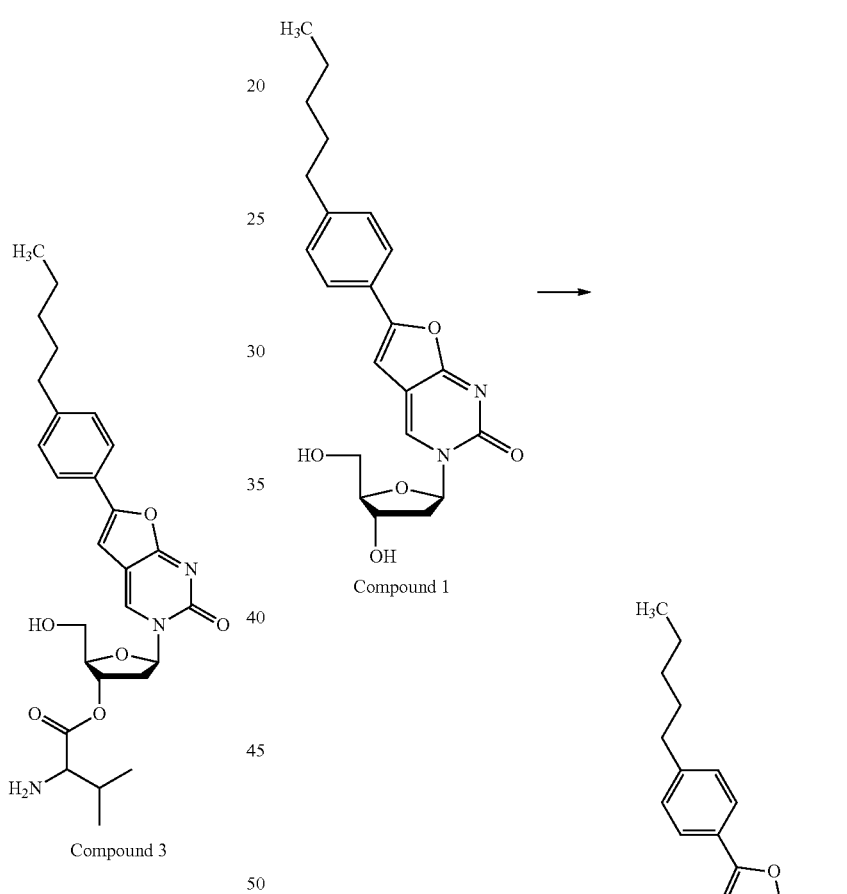

Compound 3

Compound 1

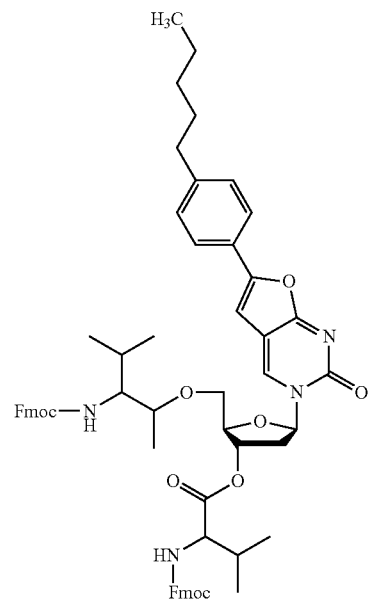

Fmoc-Compound 10

Fmoc-Compound 8 (128 mg, 0.15 mmol) was dissolved in MeOH (1 ml) and a solution of HCl 0.1N in MeOH (1.85 ml, 0.19 mmol) was added. The reaction mixture was stirred at room temperature for 2 hours and the solvent was evaporated to dryness. The residue was dissolved in dichloromethane (40 mL) and washed with a 10% aqueous NaHCO$_3$ (3×20 mL). The organic layer was dried, filtered and evaporated to dryness. The residue was dissolved in DMF (3 mL), piperidine (0.15 ml, 1.5 mmol) was added and stirred at room temperature for 5 minutes. The solvent was removed under reduced pressure and the residue was purified by CCTLC on the Chromatotron (dichloromethane/methanol, 20:1) to yield 58 mg (76%) of fully deprotected Compound 3 as a yellow oil.

$^1$H NMR (300 MHz, DMSO-d$_6$): δ 0.80-0.91 (m, 9H, γ-CH$_3$, Val, CH$_3$), 1.28 (m, 4H, 2CH$_2$), 1.58 (m, 2H, CH$_2$), 1.87 (m, 1H, β-CH, Val), 2.30 (m, 1H, H-2'a), 2.55-2.72 (m, 3H, CH$_2$, H-2'b), 3.17-3.73 (m, 3H, 2H-5', α-CH, Val), 4.15 (m, 1H, H-4'), 5.25 (m, 1H, H-3'), 5.32 (t, 1H, 5'-OH, J=5.2 Hz), 6.22 (t, 1H, H-1', J=6.1 Hz), 7.21 (s, 1H, H-5), 7.31 y 7.72 (AA'BB' system, 4H, Ar, J=8.3 Hz), 8.78 (s, 1H, H-4).

MS (ESI+): m/z 498.3 (M+1$^+$).

Example 8

Preparation of Fmoc-Compound 10

Formation of 3',5'-Valine Ester

3-[2'-Deoxy-3',5'-bis-O—[N-(fluorenilmethoxycarbonyl)-valyl]-β-D-ribofuranosyl]-6-(p-pentylphenyl)-2,3-dihydrofuro[2,3-d]pyrimidin-2-one To a solution of Compound 1 (188 mg, 0.47 mmol) in DMF (4 mL) at 0° C., 4-dimethylaminopyridine (17 mg, 0.14 mmol), Fmoc-Val-OH (481 mg, 1.42 mmol) and N,N'-dicyclohexyl-carbodiimide DCC (292 mg, 1.42 mmol) were successively added. The reaction mixture was stirred at room temperature for 15 hours. The white solid was filtered, washed with DMF and the solvent was evaporated to dryness. The residue, thus obtained, was dissolved in ethyl acetate (40 mL), washed with 10% aqueous citric acid (3×20 mL), 10% aqueous NaHCO$_3$ (3×20 mL), water (3×20 mL) and brine (3×20 mL). The organic layer was dried (Na$_2$SO$_4$), filtered and evaporated to dryness. The final residue was purified by flash column chromatography on silica gel (hexane/ethyl acetate, 3:1) to give 343 mg (70%) of Fmoc-Compound 10 as a white foam.

$^1$H NMR (400 MHz, acetone-d$_6$): δ 0.88 (t, 3H, CH$_3$, J=6.9 Hz), 0.91-1.02 (m, 12H, 2γ-CH$_3$, Val-3', Val-5'), 1.30-1.34 (m, 4H, 2CH$_2$), 1.57-1.64 (m, 2H, CH$_2$), 2.14-2.27 (m, 2H, β-CH, Val-3', Val-5'), 2.48 (m, 1H, H-2'a), 2.61 (t, 2H, CH$_2$, J=7.8 Hz), 2.78-2.82 (m, 1H, H-2'b), 4.18-4.61 (m, 11H, 2CH$_2$, Fmoc-3', Fmoc-5', 2CH, Fmoc-3', Fmoc-5', 2H-5', H-4', 2α-CH, Val-3', Val-5'), 5.45 (m, 1H, H-3'), 6.33 (t, 1H, H-1', J=5.9 Hz), 6.97-7.03 (m, 2H, NH, Val-3', Val-5'), 7.07 (s, 1H, H-5), 7.24-7.85 (m, 16H, Ar, Fmoc), 7.19 y 7.58 (AA'BB' system, 2H, Ar, J=8.2 Hz), 8.54 (s, 1H, H-4).

MS (ESI+): m/z 1041.3 (M+1$^+$).

Elemental analysis: calcd (%) for C$_{62}$H$_{66}$N$_4$O$_{11}$: C, 71.38; H, 6.38; N, 5.37. found: C, 71.12; H, 6.51; N, 5.50.

Example 9

Deprotection of Fmoc-Compound 10

3-[2'-Deoxy-3',5'-bis-O-valyl]-β-D-ribofuranosyl]-6-(p-pentylphenyl)-2,3-dihydrofuro[2,3-d]pyrimidin-2-one

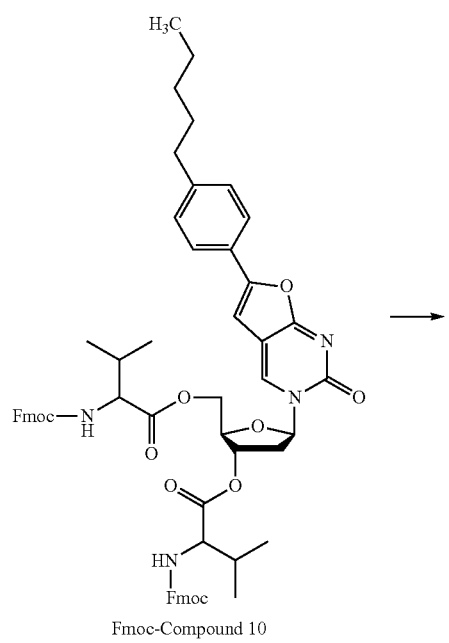

Fmoc-Compound 10

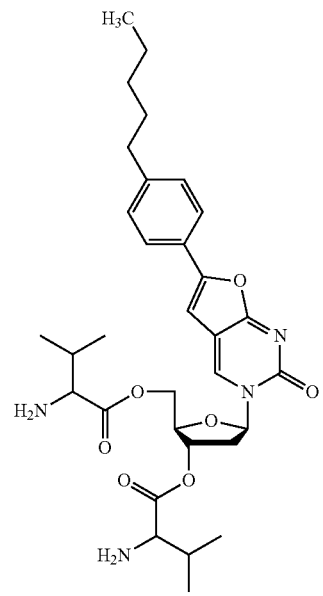

Compound 10

To a solution of Fmoc-Compound 10 (330 mg, 0.32 mmol) in DMF (12 ml) piperidine (0.6 ml, 6.0 mmol) was added and the mixture was stirred for 5 minutes. The solvent was evaporated to dryness. The residue was purified by CCTLC on the Chromatotron (dichloromethane/methanol, 20:1) to afford 181 mg (95%) of Compound 10 as a yellow oil.

$^1$H NMR (300 MHz, acetone-d$_6$): δ 0.81-0.99 (m, 15H, 2γ-CH$_3$, Val-3', Val-5', CH$_3$), 1.29-1.36 (m, 4H, 2CH$_2$), 1.62-1.67 (m, 2H, CH$_2$), 1.91-2.07 (m, 3H, 2β-CH, Val-3', Val-5', H-2'a), 2.44 (m, 1H, H-2'b), 2.67 (t, 2H, CH$_2$, J=8.1 Hz), 4.31-4.50 (m, 5H, 2H-5', H-4', 2α-CH, Val-3', Val-5'), 5.38 (m, 1H, H-3'), 6.32 (t, 1H, H-1', J=6.2 Hz), 7.07 (s, 1H, H-5), 7.34 y 7.74 (AA'BB' system, 4H, Ar, J=8.3 Hz), 8.65 (s, 1H, H-4).

MS (ESI+): m/z 597.3 (M+1$^+$), 1193.7 (2M+1$^+$).

Example 10

Preparation of Fmoc-Compound 11; Formation of 3',5'-Fmoc-Val-Pro-Val Conjugate

3-[2'-Deoxy-3',5'-bis-O-[N-(fluorenilmethoxycarbonyl)-valyl-prolyl-valyl]-β-D-ribofuranosyl]-6-(p-pentylphenyl)-2,3-dihydrofuro[2,3-d]pyrimidin-2-one

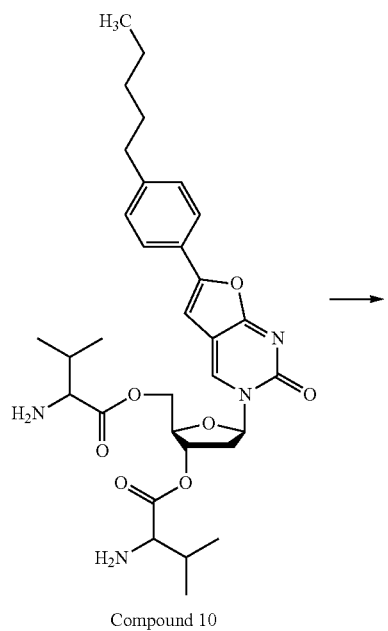

Compound 10

Following the method described in Example 1 for the synthesis of Fmoc-compound 7, a solution of compound 10 (113 mg, 0.19 mmol) in dichloromethane (5 ml) was successively reacted with Fmoc-Val-Pro-OH (198 mg, 0.45 mmol), BOP (201 mg, 0.45 mmol) and triethylamine (0.063 ml, 0.45 mmol). After the work-up the final residue was by CCTLC on the Chromatotron (dichloromethane/methanol, 40:1) to afford 184 mg (68%) of Fmoc-compound 11 as a yellow oil.

$^1$H NMR (300 MHz, acetone-d$_6$): δ 0.86-1.05 [m, 27H, 4γ-CH$_3$, (Val$_1$, Val$_2$)-3' y (Val$_1$, Val$_2$)-5', CH$_3$], 1.30 (m, 4H, 2CH$_2$), 1.62 (m, 2H, CH$_2$), 1.91-2.55 [m, 14H, 2H-2', 4β-CH, (Val$_1$, Val$_2$)-3' and (Val$_1$, Val$_2$)-5', 2β-CH$_2$, Pro-3', Pro-5', 2γ-CH$_2$, Pro-3', Pro-5'], 2.64 (m, 2H, CH$_2$), 3.58-3.84 (m, 4H, 2δ-CH$_2$, Pro-3', Pro-5'), 4.24-4.60 (m, 15H, 2CH$_2$, Fmoc-3', Fmoc-5', 2CH, Fmoc-3', Fmoc-5', 2H-5', H-4', 4α-CH, (Val$_1$, Val$_2$)-3' and (Val$_1$, Val$_2$)-5', 2α-CH Pro-3', Pro-5'), 5.46 (m, 1H, H-3'), 6.65 (m, 1H, H-1'), 7.19 (s, 1H, H-5), 7.33-7.88 (m, 16H, Ar Fmoc), 7.34 y 7.86 (AA'BB' system, 4H, Ar, J=7.5 Hz), 8.70 (s, 1H, H-4).

MS (ESI+): m/z 1434.4 (M+1$^+$).

Example 11

Preparation of Compound 11; Deprotection of 3',5'-Fmoc-Val-Pro-Val Conjugate 3-(2'-Deoxy-3',5'-bis-O-valyl-prolyl-valyl-β-D-ribofuranosyl)-6-(p-pentylphenyl)-2,3-dihydrofuro[2,3-d]pyrimidin-2-one

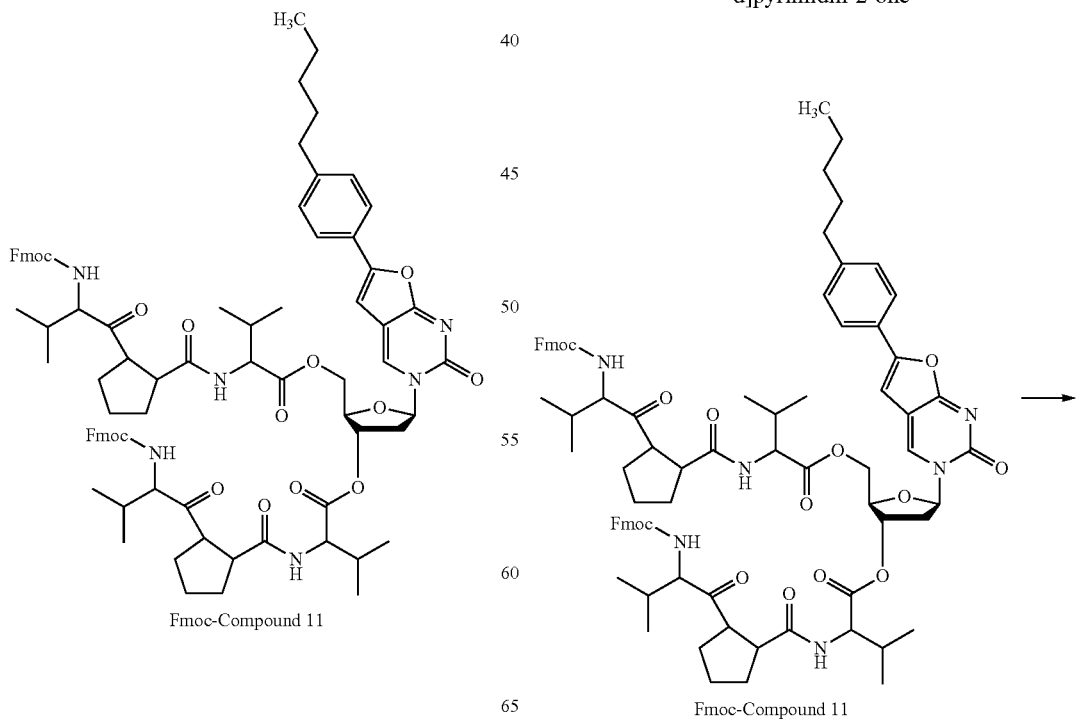

Fmoc-Compound 11

-continued

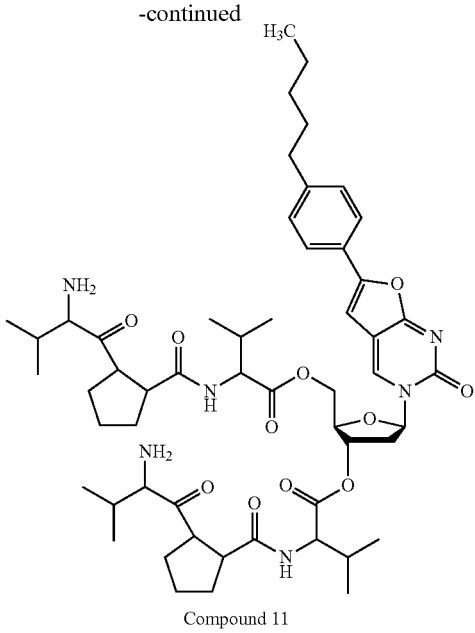

Compound 11

To a solution of Fmoc-compound 11 (164 mg, 0.11 mmol) in DMF (12 ml), piperidine (0.25 ml, 2.5 mmol) was added and the mixture was stirred for 5 minutes. The solvent was evaporated to dryness. The residue was purified by CCTLC on the Chromatotron (dichloromethane/methanol, 10:1) to afford 98 mg (87%) of compound 11 as a yellow foam.

$^1$H NMR (300 MHz, acetone-$d_6$): δ 0.88-1.02 [m, 27H, 4γ-$CH_3$, ($Val_1$, $Val_2$)-3', ($Val_1$, $Val_2$)-5', $CH_3$], 1.29-1.40 (m, 4H, 2$CH_2$), 1.65 (m, 2H, $CH_2$), 1.72-2.57 [m, 14H, 2H-2', 4β-CH, ($Val_1$, $Val_2$)-3', ($Val_1$, $Val_2$)-5', 2β-$CH_2$, Pro-3', Pro-5', 2γ-$CH_2$, Pro-3', Pro-5'], 2.67 (t, 2H, $CH_2$, J=7.7 Hz), 3.60-4.58 (m, 13H, 2H-5', H-4', 4α-CH, ($Val_1$, $Val_2$)-3', ($Val_1$, $Val_2$)-5', 2α-CH Pro-3', Pro-5', 2δ-$CH_2$, Pro-3', Pro-5'), 5.45 (m, 1H, H-3'), 6.35 (m, 1H, H-1'), 7.20 (s, 1H, H-5), 7.34 y 7.70 (AA'BB' system, 2H, Ar, J=8.1 Hz), 7.75-7.89 (m, 2H, 2NH $Val_2$-3', $Val_2$-5'), 8.68 (s, 1H, H-4).

MS (ESI+): m/z 989.5 (M+1$^+$).

Elemental analysis: calcd (%) for $C_{52}H_{76}N_8O_{11}$: C, 63.14; H, 7.74; N, 11.33. found: C, 63.27; H, 7.69; N, 11.50.

Example 12

Oral Bioavailability of Compound 1, Compound 5 and Compound 7 in Mice

A study was conducted with Compounds 1, 5 and 7 to compare the relative bioavailability of Compound 1 after oral dosing in mice. Three groups of female mice received equimolar doses of Compound 1 (25 mg/kg), 5 (31.25 mg/kg; equivalent to 25 mg/kg of Compound 1) or 7 (41.8 mg/kg; equivalent to 25 mg/kg of compound 1) as a single oral gavage dose formulated in 0.5% carboxymethylcellulose. The mice were serially sacrificed at time-points ranging from 0.25 to 3 hours post dosing (3 mice/time-point), and plasma samples were taken and analyzed for Compound 1 concentration using a non-validated HPLC method with fluorescence detection. Results are reported as relative peak areas for Compound 1, which assumes that peak area is directly proportional to concentration over these ranges of concentrations.

The results of this study are shown in Table 1 below and in FIG. 1 of the accompanying drawings. Plasma concentrations of Compound 1 were much higher in mice receiving Compounds 5 and 7 as compared to mice receiving Compound 1. Note that although these data do not provide absolute plasma concentrations of Compound 1, one can estimate from the peak areas that Compound 5 increases the oral bioavailability of Compound 1 by approximately 8-fold and Compound 7 by approximately 12-fold (as estimated by the AUC values).

In conclusion, this data supports the hypothesis that Compound 7 according to the present invention is a prodrug of Compound 1, and greatly increases the oral bioavailability of Compound 1.

TABLE 1

| Time (min) after | Compound 1 in plasma (area under the curve (HPLC)) | | |
|---|---|---|---|
| oral gavage | Compound 7 | Compound 5 | Compound 1 |
| 15 | 32 | 18 | 2.6 |
| 30 | 52 | 19 | 2.9 |
| 45 | 87 | 39 | 4.0 |
| 60 | 44 | 42 | 4.2 |
| 120 | 14 | 28 | 2.5 |
| 180 | 6.2 | 8.1 | 3.4 |

In all cases, only Compound 1 was detected in plasma.
Compound 5 was markedly more bioavailable than Compound 1.
Compound 7 was more bioavailable than Compound 5.

Example 13

Conversion of Compound 7 by Purified CD26, Bovine Serum (10%) and Human Serum (10%)

A variety of test compounds have been evaluated for their substrate activity against purified CD26, human serum (HS), and bovine serum (BS) in Eppendorf tubes. The 400 μL reaction mixture contained 50 μM of test compound in PBS (containing 0.1% DMSO). The reaction was started by the addition of purified CD26 (1.5 mU) or 20% of HS (in PBS) or BS (in PBS) at 37° C. At different time points, 100 μL was withdrawn from the reaction mixture, added to 200 μL methanol, and put on ice for ~10 min. Then, the mixture was centrifuged at 13,000 rpm for 5 min at 4° C. and 250 μL of supernatant was analyzed by HPLC on a reverse phase RP-8 column, using following gradients:

Gradient A (Buffer A: 50 mM $NaH_2PO_4$+5 mM heptane-sulfonic acid pH 3.2; buffer B: acetonitrile): 2 min 98% A+2% B; 6 min linear gradient to 80% A+20% B; 2 min linear gradient to 75% A+25% B; 2 min linear gradient to 65% A+35% B; 18 min linear gradient to 50% A+50% B; 5 min 50% A+50% B; 5 min linear gradient to 98% A+2% B; 5 min equilibration at 98% A+2% B.

Gradient B: 2 min 98% A+2% B; 6 min linear gradient to 80% A+20% B; 2 min linear gradient to 75% A+25% B; 2 min linear gradient to 65% A+35% B; 8 min linear gradient to 50% A+50% B; 10 min 50% A+50% B; 10 min linear gradient to 20% A+80% B; 5 min 20% A+80% B; 15 min linear gradient to 98% A+2% B; 5 min 98% A+2% B.

TABLE 2

Conversion of Compound 7 to Compound 5 and Compound 1 in vitro

| | | Formation of hydrolysis products (%) | | |
|---|---|---|---|---|
| | Time (hr) | Compound 7 | Compound 5 | Compound 1 |
| CD26 | 0 | 100 | 0 | 0 |
| | 2 | 0 | 50.6 | 49.4 |

TABLE 2-continued

Conversion of Compound 7 to Compound 5 and Compound 1 in vitro

| | Formation of hydrolysis products (%) | | | |
|---|---|---|---|---|
| | Time (hr) | Compound 7 | Compound 5 | Compound 1 |
| | 6 | 0 | 37.1 | 62.9 |
| | 20 | 0 | 24.5 | 75.5 |
| Bovine serum 10% | 0 | 100 | 0 | 0 |
| | 1 | 59.8 | 19.9 | 20.3 |
| | 4 | 20.4 | 34.7 | 44.8 |
| | 20 | 3.3 | 21 | 74.4 |
| Human serum 10% | 0 | 100 | 0 | 0 |
| | 1 | 31 | 11.4 | 57.6 |
| | 4 | 5.0 | 21.5 | 73.4 |
| | 20 | 1.8 | 9.7 | 88.5 |

Rapid conversion of Compound 7 to Compound 5 occurs in the presence of purified CD26 (1.5 mU in PBS), bovine serum (10%) and human serum (10%) in PBS.
Compound 7 is fully stable in PBS for 6 hrs at 37° C. (not shown). Compound 5 is unstable. It spontaneously degrades to Compound 1 in buffer.
Compound 5 is stabilized as a salt derivative.

Example 14

Anti-VZV Activity of Compounds 7 and 9 and Compounds 5 and 3 in Comparison with Compound 1

The objective of this study was to compare the antiviral activity of Compounds 1, 3, 5, 7 and 9 in HEL cells inoculated with VZV strains. Antiviral activity was assessed as the ability of Compounds 1, 3, 5, 7 and 9 to reduce viral plaque formation after incubation periods of 5 days as compared to untreated control cultures. The results of the antiviral efficacy studies showing comparable efficacy between the three compounds are shown in Tables 3a and 3b below.

VZV-drug susceptibility assays were performed on confluent HEL cells in 96-well microtiter plates. Monolayers were infected with 20 PFU of cell-associated virus per well. For each assay, virus controls (infected-untreated cells) were included. After a 2-hour incubation period, the virus inoculum was removed and the media replaced by the different dilutions (in duplicate) of the tested molecules. Serial dilutions of test compounds were incubated with the infected monolayers for 5 days. After the 5-day incubation period, the cells were fixed and stained with Giemsa, and the level of virus-induced cytopathic effect was determined by counting the number of plaques for each dilution. Activity was expressed as $EC_{50}$ (effective compound concentration required to reduce virus-plaque formation by 50%) compared to the untreated control.

TABLE 3

| | $EC_{50}{}^a$ (µM) | | | | |
|---|---|---|---|---|---|
| | VZV TK+ | | VZV TK− | | |
| Cmpd | YS | OKA | 07/1 | MCC (µM) | $CC_{50}$(µM) |
| 5 | 0.03 | 0.014 | >1 | >1 | >0.5 |
| 7 | 0.01 | 0.012 | >1 | >1 | >0.5 |
| 1 | 0.02 | 0.008 | >1 | >1 | >5.0 |

$^a$50% effective concentration

TABLE 3b

| | $EC_{50}{}^a$ (µM) | | | | |
|---|---|---|---|---|---|
| | VZV TK+ | | VZV TK− | | |
| Cmpd | YS | OKA | 07/1 | MCC (µM) | $CC_{50}$(µM) |
| 3 | 0.004 | 0.007 | >5 | 20 | >5 |
| 9 | 0.016 | 0.017 | >5 | 20 | >5 |
| 1 | 0.003 | 0.003 | >20 | >20 | >5 |

$^a$50% effective concentration

Compounds 7 and 9 and 5 and 3 are active in VZV-infected HEL cell cultures. They lose antiviral activity against VZV/TK−. Neither of them is cytotoxic or cytostatic at concentrations that largely exceed the antiviral concentrations.

Example 15

Water-Solubility Studies

The water-solubility of Compound 7 was determined by HPLC analysis and compared with that of Compound 5 and parent Compound 1. HPLC was carried out on a Waters 484 System using Novapack C18 reverse phase column. Flow rate: 1 mL/min. Detection: UV 254 nm. Gradient solvent system A/B (acetonitrile/water): initial 15% A+85% B; 5 min linear gradient to 25% A+75% B; 5 min linear gradient to 35% A+65% B; 10 min linear gradient to 45% A+55% B; 5 min linear gradient to 60% A+40% B and 5 min linear gradient to 100% A.

Excess amount of the prodrug or the parent drug was suspended in deionised water, sonicated for 10 min at room temperature, and then equilibrated overnight at room temperature. The samples were centrifuged at 14.000 rpm in an Eppendorf micro-centrifuge for 1.5 min at room temperature. An aliquot of the clear supernatant was removed and diluted to a concentration within the range of a five-point standard curve. Water-solubility was calculated from each peak area of the above solution by HPLC compared with the sample dissolved in acetonitrile, the concentration of which is already known.

Figure 2:
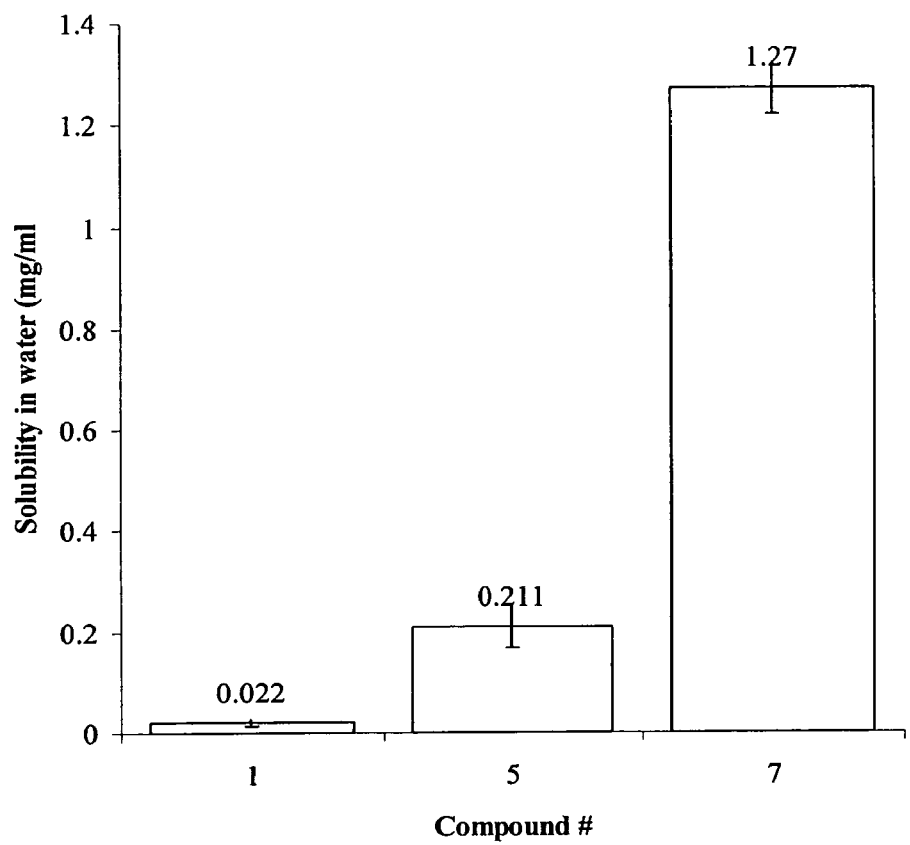
FIG. 2 shows the water-solubility of Compounds 1, 5 and 7.

The values of solubility and partition coefficients of the prodrugs and parent compound are provided in Table 4 below. Predicted partition coefficient values suggest that lipophilicity can be significantly reduced from 3.24 to 1.60 or 0.70 upon introduction of the valyl or tripeptidyl moiety. The prodrugs exhibited higher water-solubility than the parent drug as shown in FIG. 2. Compound 7 prodrug improved the water-solubility (1.27 mg/mL) more than 57-fold in comparison with the parent Compound 1 (0.022 mg/mL). This result suggests that the CD26 prodrug approach could be useful for increasing the water-solubility of hydrophobic drugs.

TABLE 4

Physicochemical properties of Compounds 1, 5 and 7

| Test Compound | Predicted logP$^a$ | Predicted logW$^a$ | Solubility in water (mg/ml)$^b$ |
|---|---|---|---|
| 1 | 3.24 | −1.97 | 0.022 ± 0.007 |
| 5 | 1.60 | −4.49 | 0.211 ± 0.044 |
| 7 | 0.70 | −7.83 | 1.27 ± 0.05 |

$^a$Predicted value of logP and logW (water solubility) was obtained using the website http://www.logp.com
$^b$Data are means of three determinations

What is claimed is:

1. A method of treatment of viral infection with the Varicella Zoster virus, comprising administering to a human or non-human animal patient in need of such treatment an effective amount of a compound of formula (III):

(III)

wherein
X is O, S, NH or $CH_2$;
Y is O, S or NH;
Z is O, S or $CH_2$;
$R_1$ is $C_{1-8}$ alkyl;
at least one of $R_2$ and $R_3$ is H—$[R_4$—$R_5]_n$—$R_6$—, in which:
H—$[R_4$—$R_5]_n$— comprises an oligopeptide,
$R_4$ is an amino acid,
$R_5$ is an amino acid selected from the group consisting of proline, alanine, hydroxyproline, dihydroxyproline, thiazolidinecarboxylic acid (thioproline), dehydroproline, pipecolic acid (L-homoproline), azetidinecarboxylic acid, aziridinecarboxylic acid, glycine, serine, valine, leucine, isoleucine and threonine,
$R_6$ is a neutral, non-polar amino acid moiety that is bonded to $R_5$ by a peptide bond, and
n is 1, 2, 3, 4 or 5; and
the other of $R_3$ and $R_2$ is H—$[R_4$—$R_5]_n$—$R_6$— or H;
or a pharmaceutically acceptable salt thereof.

2. The method of claim 1, wherein 100-500 mg of said compound is administered once daily (s.i.d.).

3. The method of claim 1, wherein said compound is administered with a pharmaceutically acceptable excipient.

4. The method of claim 1, wherein one of $R_2$ and $R_3$ is H—$[R_4$—$R_5]_n$—$R_6$— and the other is H.

5. The method of claim 1, wherein $R_2$ and $R_3$ are each H—$[R_4$—$R_5]_n$—$R_6$—.

6. The method of claim 5, wherein $R_2$ and $R_3$ are the same.

7. The method of claim 1, wherein n=1.

8. The method of claim 1, wherein $R_4$ is selected from the group consisting of alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine and valine.

9. The method of claim 1, wherein $R_5$ is selected from the group consisting of proline, alanine, glycine, serine, valine and leucine.

10. The method of claim 1, wherein said oligopeptide —$[R_4$—$R_5]$— is selected from the group consisting of Val-Pro, Asp-Pro, Ser-Pro, Lys-Pro, Arg-Pro, His-Pro, Phe-Pro, Ile-Pro, Leu-Pro, Val-Ala, Asp-Ala, Ser-Ala, Lys-Ala, Arg-Ala, His-Ala, Phe-Ala, Ile-Ala and Leu-Ala.

11. The method of claim 1, wherein said neutral, non-polar amino acid moiety $R_6$ is:

in which $R_7$, $R_8$ and $R_9$ are each independently H or $C_{1-3}$ alkyl.

12. The method of claim 11, wherein $R_9$ is H.

13. The method of claim 1, wherein $R_6$ is valine, leucine, isoleucine or alanine.

14. The method of claim 1, wherein $R_2$ and $R_3$ are each H-Val-Pro-Val-.

15. The method of claim 1, wherein X, Y and Z are each O.

16. The method of claim 1, wherein said compound has a structural formula selected from the group consisting of:

and

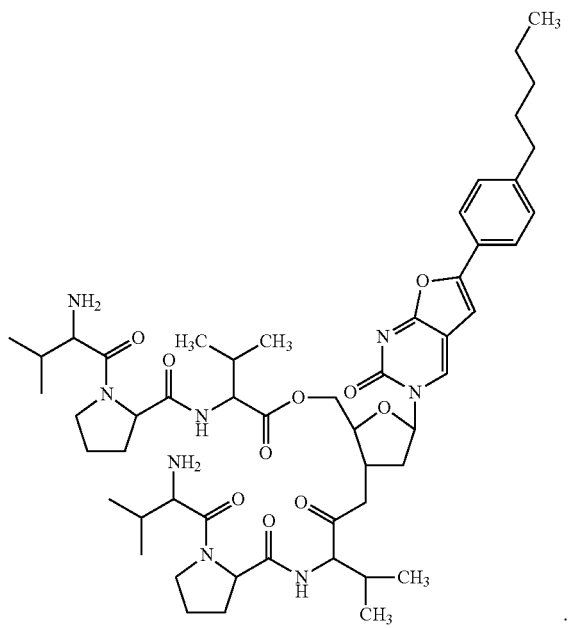 [SMILES: CCCCCc1ccc(-c2cc3cn(C4CC(CC(=O)C(NC(=O)C5CCCN5C(=O)C(N)C(C)C)C(C)C)C(COC(=O)C(NC(=O)C5CCCN5C(=O)C(N)C(C)C)C(C)C)O4)c(=O)nc3o2)cc1]

17. A method of treatment of viral infection with the Varicella Zoster virus, comprising administration to a human or non-human animal patient in need of such treatment an effective amount of a compound of formula (II):

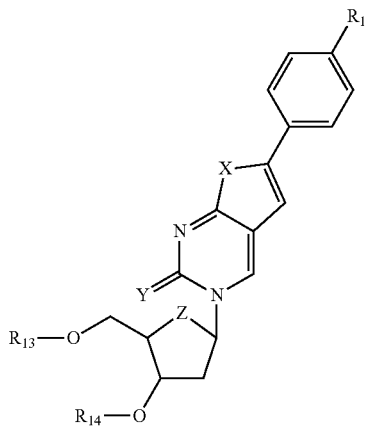

wherein
X is O, S, NH or $CH_2$;
Y is O, S or NH;
Z is O, S or $CH_2$;
$R_1$ is $C_{1-6}$ alkyl;
$R_{13}$ and $R_{14}$ are each a neutral, non-polar amino acid moiety having a free amino terminus.

18. The method of claim 17, wherein 100-500 mg of said compound is administered once daily (s.i.d.).

19. The method of claim 17, wherein said compound is administered with a pharmaceutically acceptable excipient.

20. The method of claim 8, wherein $R_4$ is valine.

21. The method of claim 9, wherein $R_5$ is proline or alanine.

22. The method of claim 13, wherein $R_6$ is valine.

* * * * *

UNITED STATES PATENT AND TRADEMARK OFFICE
CERTIFICATE OF CORRECTION

PATENT NO. : 8,912,163 B2  
APPLICATION NO. : 13/971631  
DATED : December 16, 2014  
INVENTOR(S) : Jan Balzarini Page 1 of 1

It is certified that error appears in the above-identified patent and that said Letters Patent is hereby corrected as shown below:

On the Title Page, (73) Assignee "Consejo Superior de Investigaciones Ceintificas" should read --Consejo Superior de Investigaciones Cientificas--

Signed and Sealed this
Second Day of June, 2015

Michelle K. Lee
*Director of the United States Patent and Trademark Office*